(12) United States Patent
Newberg

(10) Patent No.: US 6,821,773 B1
(45) Date of Patent: Nov. 23, 2004

(54) DRAINABLE FERRULE VALVE DESIGN

(75) Inventor: Douglas A. Newberg, Gambrills, MD (US)

(73) Assignee: NL Technologies, Ltd., Gambrills, MD (US)

( * ) Notice: Subject to any disclaimer, the term of this patent is extended or adjusted under 35 U.S.C. 154(b) by 0 days.

(21) Appl. No.: 09/688,143

(22) Filed: Oct. 16, 2000

Related U.S. Application Data

(63) Continuation-in-part of application No. 09/122,629, filed on Jul. 27, 1998, now Pat. No. 6,133,022, which is a continuation-in-part of application No. 08/613,586, filed on Mar. 12, 1996, now Pat. No. 5,786,209, which is a division of application No. 08/215,416, filed on Mar. 21, 1994, now Pat. No. 5,525,301, which is a continuation-in-part of application No. 07/911,052, filed on Jul. 9, 1992, now Pat. No. 5,296,197.

(51) Int. Cl.[7] .................................................. C12M 1/26
(52) U.S. Cl. ............................... 435/309.2; 435/286.5; 422/103; 73/863.81; 73/863.86
(58) Field of Search ........................... 435/286.5, 309.2, 435/309.1; 73/863.01, 863.02, 863.81, 863.82, 863.83, 863.85, 863.86; 137/798, 340; 251/144, 145, 143, 331, 335.2, 335.3, 114; 422/99, 100, 103, 104

(56) References Cited

U.S. PATENT DOCUMENTS

| | | |
|---|---|---|
| 982,836 A | 1/1911 | Ley et al. |
| 1,831,457 A | 11/1931 | Larsen |
| 1,910,563 A | 5/1933 | Porter |
| 1,910,909 A | 5/1933 | Werder |
| 1,970,546 A | 4/1934 | Clapper |
| 1,969,081 A * | 8/1934 | Vogel-Jorgensen ......... 73/865.5 |
| 2,012,836 A * | 8/1935 | Talbot et al. ............ 73/863.86 |
| 2,041,694 A | 5/1936 | Buckley |

(List continued on next page.)

FOREIGN PATENT DOCUMENTS

| | | | |
|---|---|---|---|
| CA | 2027465 | 10/1990 | |
| CA | 2033877 | 1/1991 | |
| GB | 1567285 | 12/1977 | |
| GB | 2220250 A * | 1/1990 | ............ G01N/1/20 |
| JP | 56-38443 A | 9/1981 | |
| JP | 58-76136 A | 5/1983 | |
| JP | 62-44644 A | 2/1987 | |
| JP | 63-265165 A | 11/1988 | |
| JP | 2-140446 A | 11/1990 | |
| JP | 2-296087 A | 12/1990 | |
| JP | 03-51740 A | 3/1991 | |
| JP | 5-118970 A | 5/1993 | |
| JP | 5-56202 A | 7/1993 | |
| JP | 54-96825 A | 7/1997 | |
| WO | WO 90/12972 A1 | 11/1990 | |

*Primary Examiner*—William H. Beisner
(74) *Attorney, Agent, or Firm*—Birch, Stewart, Kolasch & Birch, LLP

(57) ABSTRACT

An apparatus for inoculating a sample to or withdrawing a sample from a vessel or conduit includes a body with an internal sample cavity, a valve operating rod movable to open and close an orifice to the sample cavity and a coupler to attach the body to a port of the vessel or conduit. A portion of the sample cavity is formed by an endcap which includes the orifice. The sample cavity is thermally and/or electrically insulated from the vessel or conduit. This insulation can arise from an empty or filled space between an inner wall and outer wall of the valve. Otherwise, insulating material can be used in forming the valve. The valve can be mountable on the vessel or conduit such that a positive drain angle is maintained regardless of whether the ferrule to the vessel or conduit is inclined upwardly, downwardly or is horizontal.

29 Claims, 22 Drawing Sheets

U.S. PATENT DOCUMENTS

| | | | |
|---|---|---|---|
| 2,068,225 A | | 1/1937 | Brown |
| 2,197,352 A | * | 4/1940 | Terkel .................. 222/488 |
| 2,314,167 A | * | 3/1943 | Shaw .................. 604/403 |
| 2,516,097 A | * | 7/1950 | Woodham et al. |
| 2,589,712 A | | 3/1952 | Langsenkamp et al. |
| 2,830,261 A | | 4/1958 | Estelle |
| 2,844,964 A | | 7/1958 | Guibert |
| 2,934,308 A | | 4/1960 | Kaufmann |
| 2,998,990 A | | 9/1961 | Plattsmier et al. |
| 3,294,362 A | | 12/1966 | Schultz et al. |
| 3,399,695 A | | 9/1968 | Stehlin |
| 3,429,552 A | | 2/1969 | Huley et al. |
| 3,528,087 A | | 9/1970 | Perkins |
| 3,638,499 A | | 2/1972 | Saint-Andre |
| 3,747,411 A | | 7/1973 | McDermott et al. |
| 3,929,017 A | | 12/1975 | Kowalski |
| 4,022,066 A | | 5/1977 | Kaune |
| 4,096,754 A | | 6/1978 | Beveridge, Jr. et al. |
| 4,338,689 A | | 7/1982 | Zieg |
| 4,346,611 A | | 8/1982 | Welker |
| 4,405,561 A | | 9/1983 | Neale et al. |
| 4,594,904 A | * | 6/1986 | Richter .................. 73/863.86 |
| 4,669,321 A | * | 6/1987 | Meyer .................. 73/863.85 |
| 4,804,164 A | | 2/1989 | Nakazawa et al. |
| 4,815,692 A | | 3/1989 | Loiseau et al. |
| 4,822,570 A | | 4/1989 | Lerman et al. |
| 4,836,236 A | | 6/1989 | Ladisch |
| 4,909,271 A | | 3/1990 | Canaan et al. |
| 4,911,412 A | | 3/1990 | Danko |
| 5,095,765 A | | 3/1992 | Filbey et al. |
| 5,096,029 A | | 3/1992 | Bauer et al. |
| 5,152,500 A | | 10/1992 | Hoobyar et al. |
| 5,296,197 A | | 3/1994 | Newberg et al. |
| 5,525,301 A | | 6/1996 | Newberg et al. |
| 5,625,157 A | | 4/1997 | Piirainen et al. |
| 5,786,209 A | | 7/1998 | Newberg |
| 6,133,022 A | | 10/2000 | Newberg |

* cited by examiner

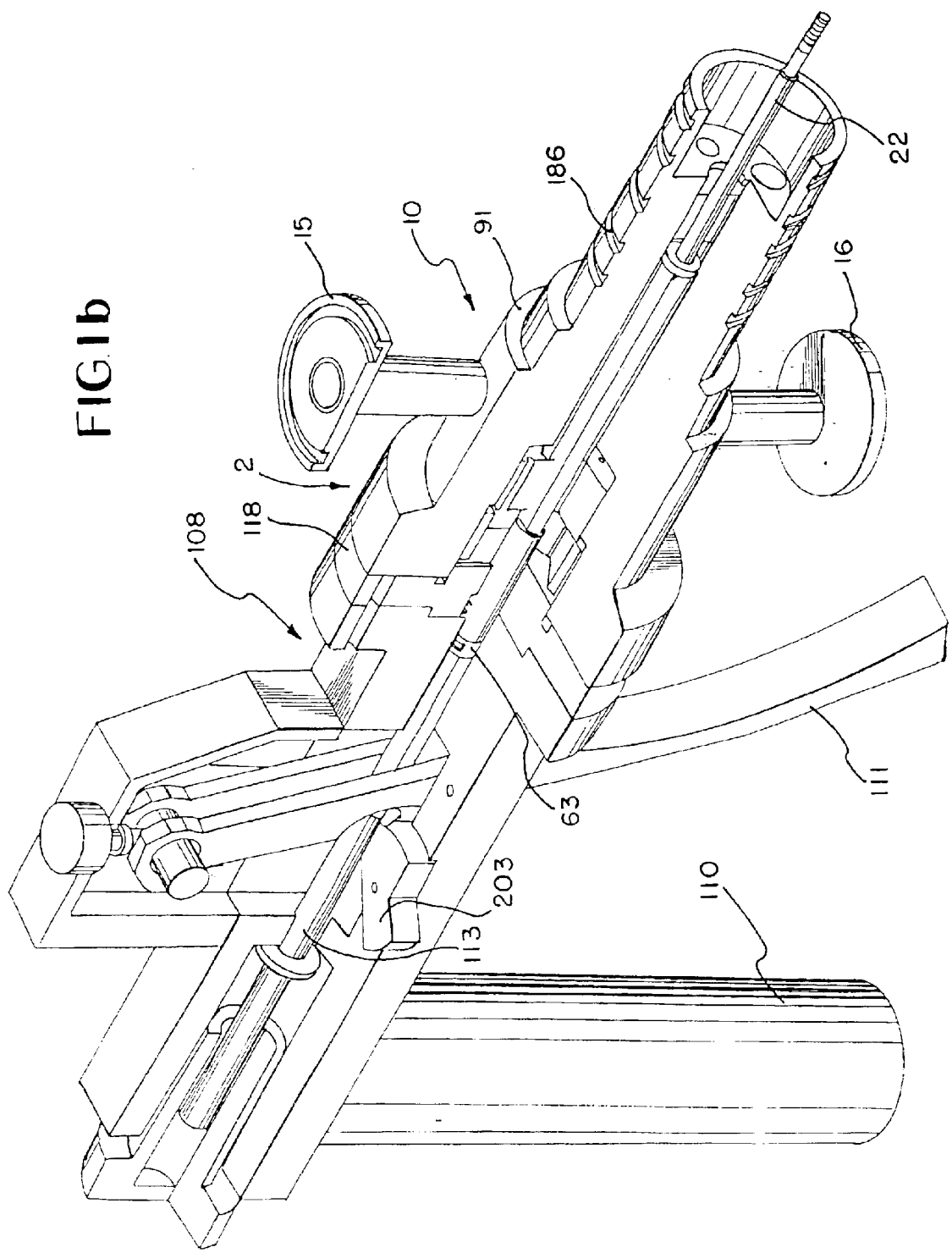

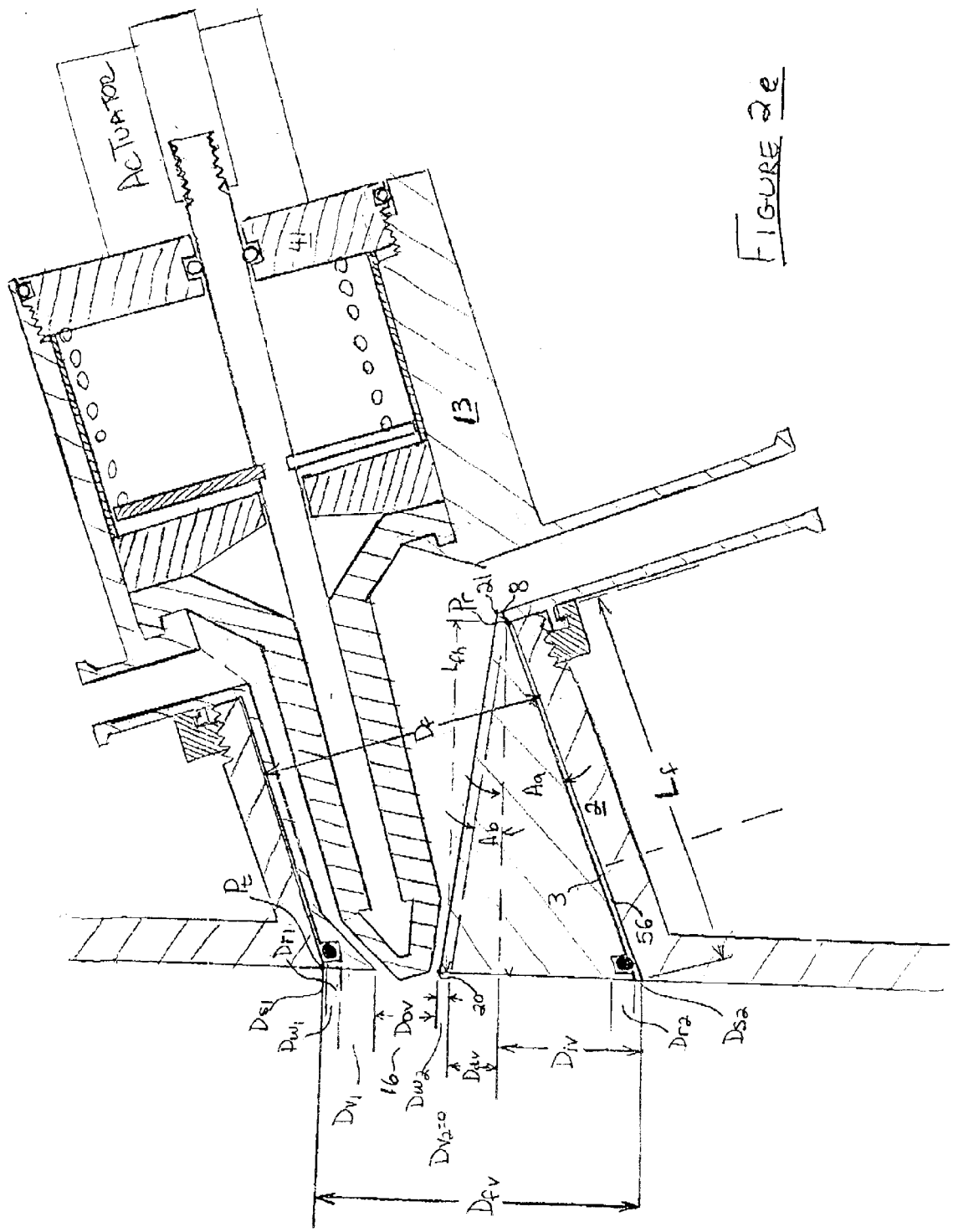

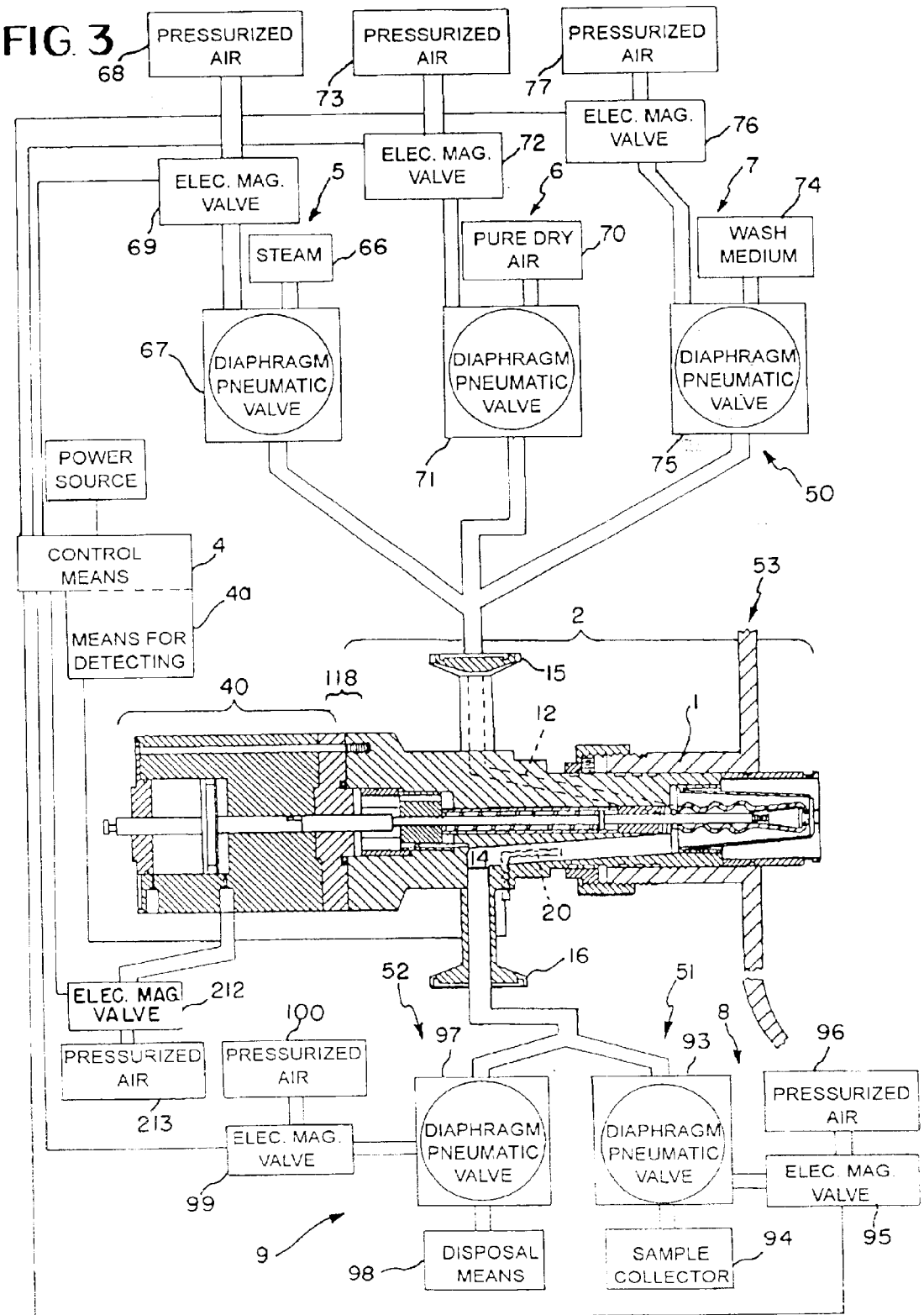

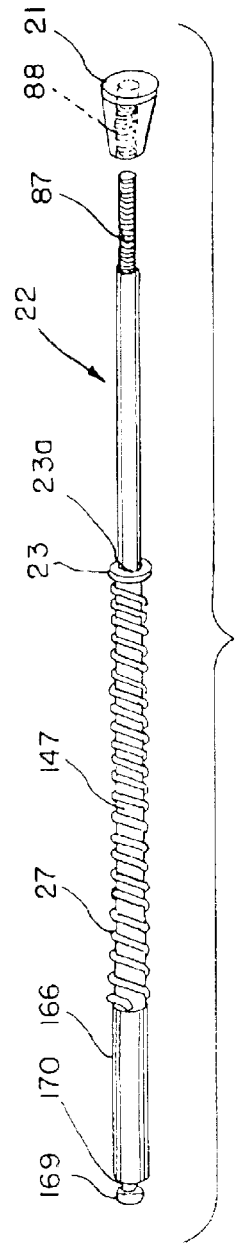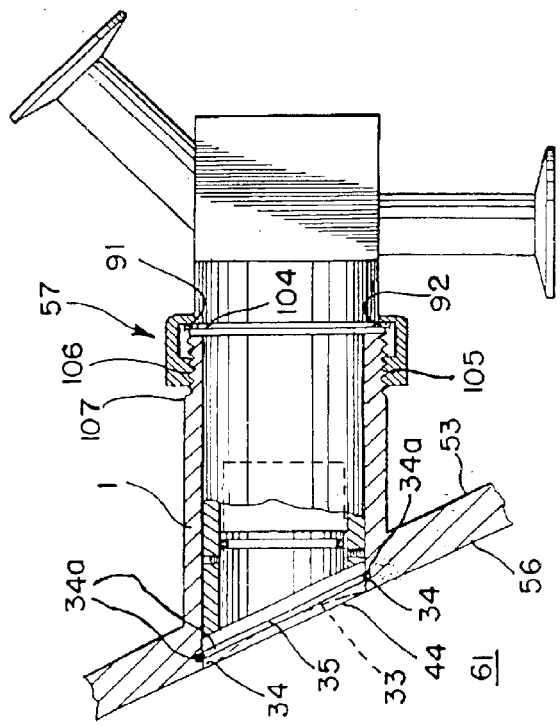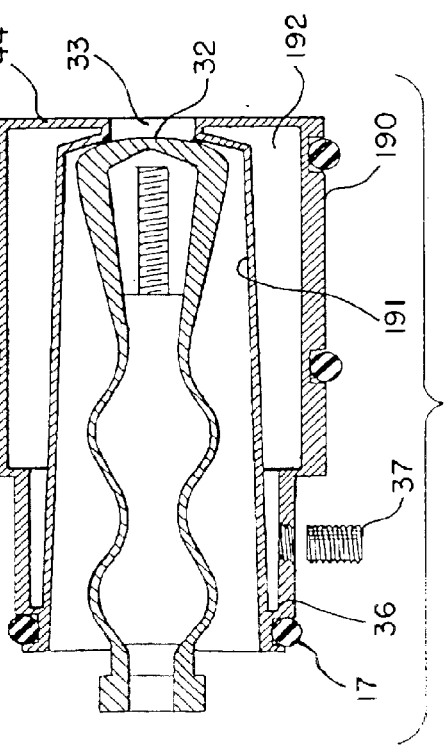

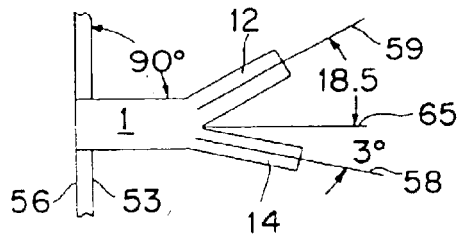
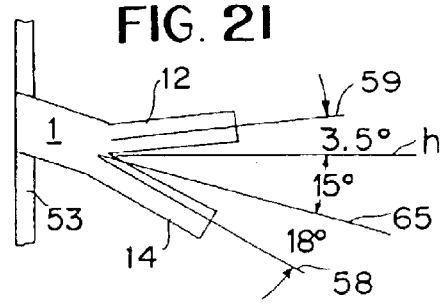
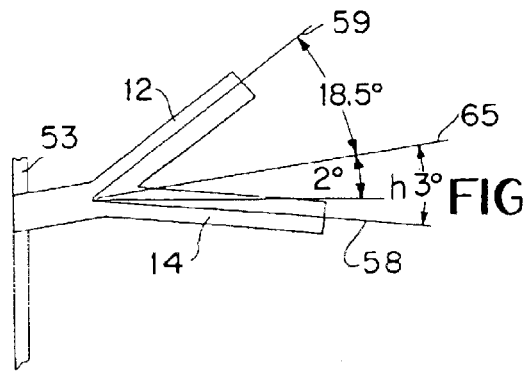
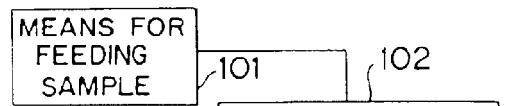
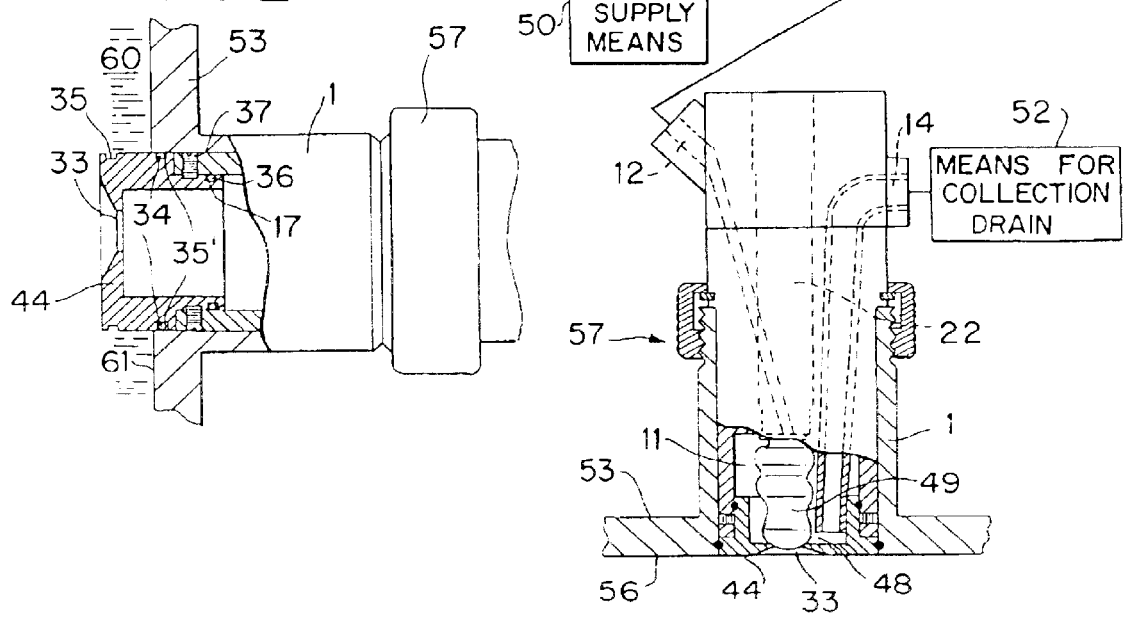

DRAINABLE FERRULE VALVE DESIGN

CROSS-REFERENCE TO RELATED APPLICATIONS

This application is a continuation-in-part of U.S. application Ser. No. 09/122,629, filed Jul. 27, 1998, now U.S. Pat. No. 6,133,022, which is a continuation-in-part of U.S. application Ser. No. 08/613,586, filed Mar. 12, 1996, now U.S. Pat. No. 5,786,209, which is a divisional of U.S. application Ser. No. 08/215,416, filed Mar. 21, 1994, now U.S. Pat. No. 5,525,301, which is a continuation-in-part of U.S. application Ser. No. 07/911,052, filed Jul. 9, 1992, now U.S. Pat. No. 5,296,197, the entire contents of each of these applications is hereby incorporated by reference.

BACKGROUND OF THE INVENTION

1. Field of the Invention

The present invention relates to an automated sample extractor or feeder/inoculator and a removable manual override operator for a vessel or conduit. This vessel or conduit can be a bioreactor or other similar equipment.

2. Description of the Background Art

Development of new or more efficient commercialization of existing products requires faster and more effective methods to measure process variables. This is particularly true in processes which require cell culture and fermentation processes conducted in bioreactors where the accuracy of measurements in the research and development are critical for achieving economic production of high purity and highly refined end products.

Some factors which must be controlled include temperature and pressure. These factors are easily measured by utilizing standard sensors. However, many other factors can be measured only by removing samples for external laboratory analysis. The frequency of sample extraction for testing and measurement, number of tests on each sample and the time constraints on the process vary widely as do the methods and equipment used to obtain the samples.

In most cases, measurement processes for variables do not lend themselves to in-situ measurement by remote sensors directly in the process. Instead, samples must be physically extracted from the process and examined and manipulated outside the vessel or conduit. Before this examination and manipulation process can be carried out, a safe, effective means of sample extraction must be made available. By "safe" here we mean that the process should remain as unaffected by the act of taking a sample as possible as the sample itself should. Besides being safe and effective, the means of sample removal should also take into consideration that the character of sample material taken from one place is very likely to differ from that taken from another place. Therefore, it is important to provide a means by which sample material can be removed from the vessel from a location where its character correlates well with information being derived from in-situ sensor measurements as well as with the character of the bulk of the process material. As such the means for removing material would best be one that also can be flexibly incorporated new or existing systems such as into existing (angled) ferrules and, at the same time, provide a means of sampling the process in the same area as is sampled by other in-situ measurement sensors.

The prior art provides for removal of sample material but does not provide features that could adequately address issues concerning the quality of the material as a representative sample of the process nor the ability to be effectively incorporated into existing system. Many of the prior art designs do not lend themselves easily to use as a retrofit but, instead, require substantial modification to the system for installation or repositioning. An apparatus should minimize or eliminate the dangers associated with the sampling process in an efficient and cost effective manner while providing quality, reproducible results in order to be of value for commercial application.

When working with samples, especially hazardous samples, it is necessary to remove or feed/inoculate material without endangering the integrity of the process, subsequently sampled material, the operator or the outside environment. Many prior art devices are unsatisfactory in this area.

Also, some prior art systems are not automated. Therefore, there is potential danger posed by human procedural errors which could easily result in operator and environmental exposure. Accordingly, a need exists for an automatable apparatus with the capacity for independent verification of equipment operation built in.

There is a need for an automated system which offers a quick, easy-to-use means to override the automation apparatus. Sampling is most important in processes of which relatively little is known. The apparatus should be one that is easily incorporated into new and existing systems in one or more places in a cost-effective way, allowing material to be removed or added to the process at multiple points so that the optimal means for monitoring and controlling the process can be established. Once defined, unnecessary or redundant devices should be easily removed from the process without adversely affecting the process but these devices should, ideally also remain intact and unaffected so that they may be readily used again in other process development, monitoring and control applications.

There always is a need to collect unanticipated samples. In providing this means, it is critical that the apparatus should be able to provide essentially identical samples in either case (i.e. manual or automated mode). Furthermore, the materials being sampled themselves are often expensive. Therefore, excessive removal of sample should be avoided. In the existing art, rotating cams and rotating knobs or handwheels are usually the means employed to open and close sampling valves. These designs require the operator to move their arm or, at least their hand, through a range of motion of 90–180 degrees or more. In the very best conditions this motion will take at least 1.0 second to perform a full cycle (open and close). Since most sample port apertures are 5 mm or more in diameter, it is very likely that 30 ml or more of process material will flow out between the time the valve is opened and closed. Usually the volume of sample required is small, often 50 ml or less.

As a consequence, one of two events occurs. Either a relatively large amount of sample material is wasted or the technician must resort to "throttling" the valve (partially opening it). Since process material is either valuable, hazardous or there is a need for cleanliness, there is a tendency of technicians to resort to throttling the valve to more carefully and accurately control the flow of sampling material. However, "throttling" can significantly alter the sample in two important ways.

First, the smaller, more fluid elements of the sample will more easily pass through the constricted opening rather than the larger, more viscous elements. The result is a selective removal, or sieving out, of the larger, more viscous elements from the sample.

Second, those elements that do pass through the crevice will have been subjected to high levels of shear, possibly significantly altering their physical and chemical properties, changing them from the desired representative subsample of process populations and conditions.

An effective means to minimize this effect will require the valve to be opened to a full open position until enough sample is drawn at which time the valve must be rapidly closed. Automated actuation using electromagnetic solenoids or pneumatic actuators which have only two position, "open" or "closed", are much more preferable over "throttling" or "positioning" actuators.

Likewise, to eliminate sample bias in a manually operated valve, a manual motion which can be rapidly translated into full articulation of the operating rod from fully "closed" to fully "opened" and back must be realized. The fastest (articulating) elements in humans, besides the eyes, are the fingers. A "flick" or w "snap" of the fingers takes a fraction of a second. Since most sample particles are much smaller than the range of motion used in a single flick of a finger, direct coupling of finger motion to actuation of the operating rod of the sampling valve presents an effective solution. Furthermore, because of the relatively small cross sectional area of sampling orifice and the relatively moderate pressures used in most (biological) manufacturing processes, little or no gear reduction will be required to overcome the tension of a "fail close" return spring operating on valve operating rod to close and form a seal at the orifice. The mechanism described here can easily and quickly be removably connected to valves with automated mechanisms. When manual sampling is necessary, trigger-action control can provide a more physically and chemically representative subsample of the process with more precise control of sampling volumes with less wasting of material.

When removing or adding material to a process, it is often desirable to maintain the aseptic integrity of the process as well as protect the surrounding environment. As such it is important that material from the previous removal or addition operation not contaminate the environment, the process or the current sample material. Loss of a sample run or contamination of the process can have extremely expensive ramifications. Therefore, it is important to add material or obtain a sample without the procedure causing contamination.

Many prior art devices permit accumulation or pooling of samples or cleansing medium. When the device is first used this may not create a problem; however, upon subsequent runs, the sample material or material added to the process through the device may be contaminated, or at least, diluted.

Additionally in the prior art, technology used for taking samples is generally unsatisfactory for feeding/inoculating the vessel or container.

SUMMARY OF THE INVENTION

Accordingly, it is a primary object of the present invention to provide an apparatus for moving flowable material either in an automated or manual fashion into a vessel or conduit (an inoculation apparatus) or to move flowable material from the vessel or conduit (a sample extractor).

It is an object of the present invention to provide an apparatus which can be retrofitted to existing standard tank port holes without requiring equipment modification.

It is the further object of the invention to provide means to retrofit the present invention into existing tanks port holes of different lengths or to be installed in a penetrating configuration, equivalent to other in-situ sensors.

Another object of the present invention is to provide an apparatus which will provide a representative subsample of the process composition which will better correlate with in-situ sensor measurements, even in applications involving heat labile or electrically sensitive materials.

It is a further object of this invention to provide an automated and manual means of sampling the process, the results of either being of equivalent quality and equally being representative of the process.

It is also an object of the invention to provide a means by which manual and automated operators can be added, removed or exchanged from the valve while it is in service and without jeopardizing the aseptic integrity of either the process or the outside environment.

Another object of the invention is to provide a device that has a safety catch so that the valve cannot accidentally be opened.

Furthermore, it is an object of the invention to provide within the same means a way to lock the valve in the open position to facilitate the taking of large volume of samples.

A further object of the apparatus is to provide a means by which samples can be safely and reliably taken automatically without having to worry about injury to someone who could be caught unaware standing near or up against the device when it automatically actuates. A corollary to this is that blockage to the mechanical elements and interference with sample taking is also avoided.

Still another object of the present invention is to eliminate or minimize the dangers of the sampling process such as contamination of the sample, process or surrounding environment.

It is a further object of the present invention to provide an apparatus which will conduct a sampling and maintain the sample in sealed arrangement such that there will be no danger to the sample itself or to the operator, the process and the surrounding environment.

Another object of the present invention is to provide an automatable system to eliminate operator error.

It is the object of the invention to provide means for effectively duplicating automated action in a manual override mechanism.

Yet another object of the present invention is to provide for a built-in verification of proper operation of the apparatus.

Still another object of the present invention is to provide a sample apparatus which avoids contact of the sample with dynamic (sliding or rotating) seals, thereby avoiding potential sites for accumulation of carryover contaminants.

A further object of the present invention is to eliminate the usual static crevice areas which may collect contaminates but yet are inaccessible to cleaning and sterilization agents and thus eliminates areas which might harbor carryover contaminants.

It is a further object of the present invention to avoid dead (stagnant) spaces in the apparatus which would result in samples that are not truly reflective of the process.

Yet another object of the present invention is to avoid obstacles or barriers to free drainage of the samples, not only when the device is installed in portholes with down-sloping or horizontal interior axes of orientation but also even when the device is installed in portholes with positive interior axes of orientation relative to horizontal.

Another object of the present invention is to provide a relationship that relates the diameter of the valve sampling orifice to the angle of orientation of the porthole's internal axis with horizontal, the porthole's internal diameter and the length of the porthole's internal bottom margin, providing a means to design valves to fit in existing portholes while maintaining the capability to be free-draining as does the invention in its latest embodiment.

Still another object of the present invention is to provide a flushing arrangement for the apparatus whereby contaminants and other material will be forced from the system.

Yet a further object of the present invention is to avoid excess process void volume inside the apparatus which would result in sample volume measurement difficulties and material wastage.

Still another object of the present invention is to avoid passive "breathing" between the seals of the apparatus and the outside environment.

Another object of the present invention is to provide an apparatus which can be repeatedly cleaned and/or sterilized in place.

A further object of the invention is to provide a means by which samples can be extracted from within the body of the process closer to where the sensors take their readings rather then at the margins (of vessels or conduits) where samples are taken as when using prior art devices.

It is an additional object of the invention to minimize the amount of thermal and/or electrical exchanged between the apparatus and the process within the vessel or conduit, especially during heat sterilization cycles, even though the device may be installed in a configuration where in the sampling orifice may be positioned well within the body of the process fluid.

Yet another object of the present invention is to provide an apparatus which can easily be removed and quickly disassembled for maintenance, including replacement of worn parts.

A further object of the present invention is to provide an apparatus whose materials are compatible with the sample materials and the process.

Yet another object of the present invention is to provide a low cost apparatus which can effectively carry out sampling or inoculation.

Still another object of the present invention is to provide an apparatus which will be reliable, easy to maintain and low cost.

Another object of the present invention is to provide multiple use capability of the apparatus including feeding/inoculation as well as sampling.

These and other objects of the present invention are fulfilled by providing an apparatus for moving a sample of flowable material through a port in a wall of a vessel or conduit. Thus, this apparatus can either feed in or withdraw materials.

The apparatus comprises a body having an internal cavity with an end wall and an orifice in that end wall. The valve body, walls near the end wall and the endwall, itself, may be at least one of hollow or coated or fabricated of at least one of a thermally or electrically insulating material. The purpose of the hollow, coated or insulating material character being one of isolating the thermal and/or electrical internal valve sterilization and/or operating process from the heat and/or electrically sensitive process material it may (from time to time) come into contact with. Means (a threaded collar or clamp, for example) which is fixed or adjustable in position along the body is provided for coupling the body to the port in the vessel or conduit. Where isolation of the process from the valve components is necessary, a diaphragm valve is positioned within the internal cavity of the body. Where a diaphragm is necessary to isolate the process, it would incorporate a sealing tip to close off the sampling orifice, said sealing tip being connected to and continuos with a flexing diaphragm which can be removably anchored to the valve body so as to isolate the mechanical components and crevices from the process, two embodiments of the diaphragm valve being one with a diaphragm with a (blind) bulbous tip and a rubber bellows with a tubular body and a blunt sealing tip or one with a long shaft with a (blind) blunt sealing tip at one end and a (conical) flexing base at the other. The tip of the diaphragm can be moved to close or open the orifice. The body of the valve is spaced from the interior surfaces of the internal cavity to thereby define a sample cavity. This-sample cavity is communicable with the orifice. A valve operating rod is attached to the blunt sealing tip and is moved by an appropriate drive to open and close the orifice.

The valve operating rod extends out the rear of the valve through a plate attached to the rear wall of the valve. This plate (may) include seals that isolate the valve interior from the outside environment.

A manual valve actuator, including a leverage adjustable trigger mechanism, a safety catch, a secondary return spring with spring tension adjustment and a stroke-limiting backstop, may be removable connected to the valve body and operating rod at the back of the valve. An automated actuator can also be removable added at the same point with the trigger mechanism being removed and, if desired, reattached onto the rear wall of the automated actuator. The valve operation, therefore, can be either manually or automatically driven, the manual method being one of a finger controlled trigger action mechanism while the automated method being one employing a pneumatic, electromagnetic or other acceptable means of actuation. The results in all cases are essentially the same back and forth articulation of the valve operating rod resulting in opening and closing of the valve.

An inlet passage leads to the sample cavity of the body. In some instances where cleaning and sterilizing can be performed through the sampling orifice, the inlet passage may be eliminated. In practice, if it is present, a restriction is that it also unobstructedly drain down to the drain hole and be connected with the internal cavity.

A drainage trough (or channel) formed in the (anterior portion of the) body leads away from the orifice in the sample cavity of the body to some lowest point within the internal cavity from which material may be drained out of the cavity. The bottom of this channel forms a path between the orifice and the drain opening, the path having an angle or angles of declination to it so that, when installed in a ferrule, the angle of declination of the path is always greater than that of the ferrule. The sides and the rear wall of the internal cavity all have unobstructed paths that drain down to the drain opening exiting the valve which, when in combination with the forward drainage trough lead down to the drain opening lowest point in the internal cavity and form a drainage basin with unobstructed drainage capabilities over a wide range of installation angles. This drain trough or channel has a longitudinal axis which is noncoaxial with the longitudinal axis of the portion of the valve body which can be inserted into the porthole.

In one arrangement, steam, air and/or a wash medium can be supplied through the inlet passage, sample cavity and out the drain passage in order to clean the interior of the apparatus. With the tip of the valve moved to open the orifice, the sample can then be extracted from the vessel or conduit through the sample cavity and out the drain passage. This sample will be fed to means for collecting the sample.

When the apparatus is used for feeding or inoculating, material is normally fed through the inlet passage. This diaphragm valve is retracted and the feed or inoculate is forced through the inlet passage, past the diaphragm valve into the vessel or conduit.

In some case only one passage into or out of the valve is necessary in addition to the orifice. In these cases the washing and sterilizing of the valve can be done through the orifice at the beginning and end of the process or, in the case of feeding, by making use of the drain passage by reversing flows as necessary.

If, when the adjustable collar is positioned part way forward along the barrel of the valve and the tip of the valve is flush with the inside wall of the vessel, the collar may be repositioned all the way back on the barrel of the valve and reinserted into the ferrule. Now the secondary o-ring in the valve cap forms the seal with the ferrule and the tip of the valve will protrude beyond the margins of the vessel into the body of the process in a fashion similar to that of in-situ sensors. Since this is the region where the sensors take their readings, taking samples from this area will correlate better with sensor readings. Alternatively there may only be one o-ring groove along the barrel and the valve may always be installed in a protruding fashion or, if the user does not need to remove the device, the barrel may be permanently affixed into the wall of the vessel or conduit in either the flush or protruding fashion, thereby eliminating the need for the o-ring groove and the adjustable collar.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1b is a perspective, sectional view showing the apparatus of the present invention without the endcap of the valve body;

FIG. 2e shows the variables used to design a valve for retrofit into an existing ferrule, particularly an inclined ferrule;

FIG. 2g is a side cross sectional view similar to FIG. 2f, but with a portion of the valve housing above the drain passage removed;

FIG. 3 is a schematic view of the apparatus of the present invention used as an extractor;

FIG. 8 is an exploded side view of the valve operating rod and valve operating rod cap;

FIG. 9 is an end view of the valve operating rod;

FIG. 10 is an end view of the valve operating rod cap;

FIG. 11 is a side, sectional view showing the endcap of the valve body;

FIG. 12 is a side, partial sectional view of the apparatus of the instant invention showing the means for coupling the apparatus to a ferrule of an apparatus or conduit, an end cap of a valve subassembly being omitted for clarity;

FIG. 20 is a schematic view of the present invention attached to a generally horizontal ferrule;

FIG. 21 is a schematic view of the instant invention showing the apparatus connected to a downwardly sloping ferrule;

FIG. 22 is a schematic view of the instant invention showing the apparatus attached to an upwardly sloping ferrule;

FIG. 23 is a schematic view of the instant apparatus used as a feeder/inoculator;

FIG. 24 is a view similar to FIG. 13 showing the apparatus extending beyond the interior wall of the vessel or conduit;

DETAILED DESCRIPTION OF THE PREFERRED EMBODIMENTS

Figure 1A:
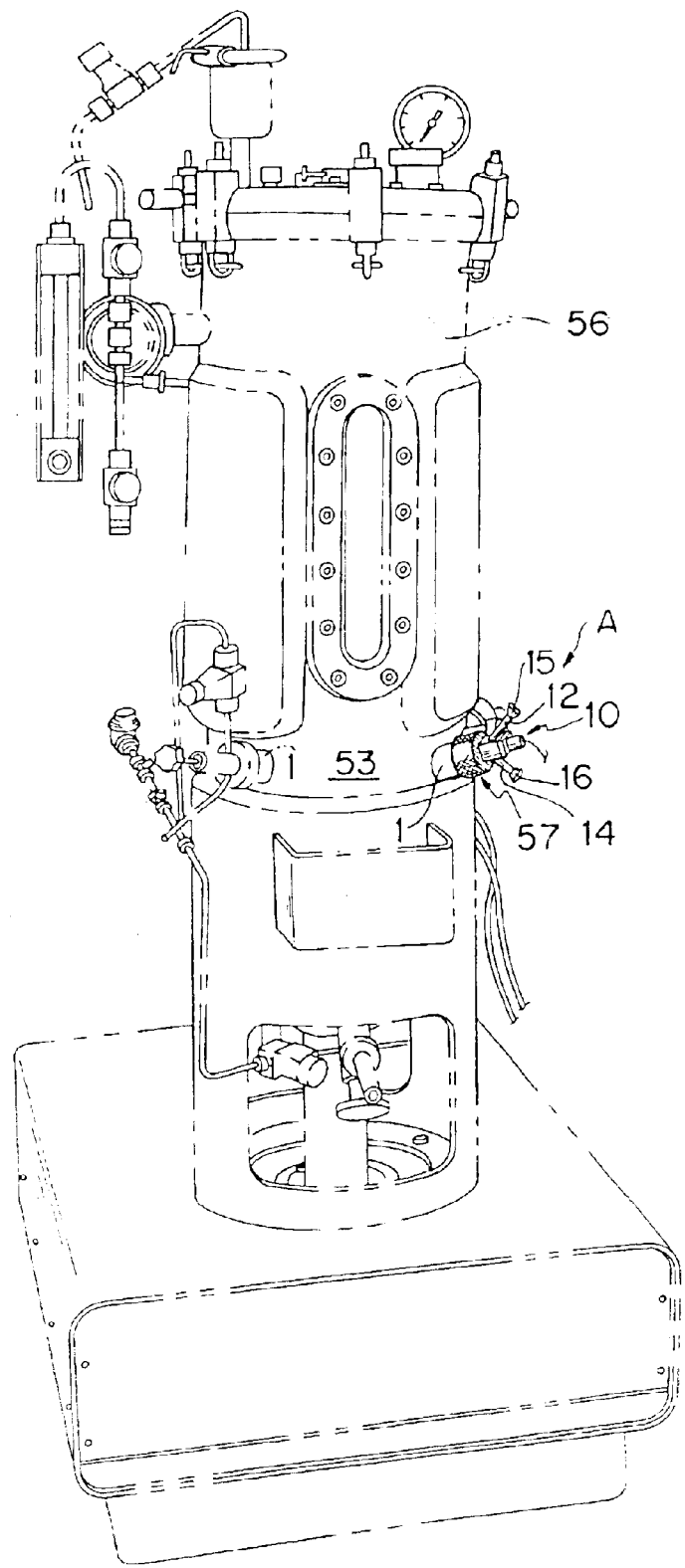
FIG. 1a is a perspective view showing the apparatus of the present invention attached to a vessel.

In the context of these discussions, "ferrule' and "porthole" may be used interchangeably. Furthermore, throughout these discussions a ferrule is discussed as though it had a round cross section with a uniform concentric central throughbore terminating on the process side (front) flush with the interior vessel or conduit wall. Also through out these discussion an example is used where in all parts are aligned in a plane that forms a vertical cross section through the assembly. All of these cases are selected both because they are the simplest arrangement to understand and would probably also be the most likely arrangement to be used. It should be understood, however, that many other related arrangements will become obvious once the design concepts and associated equations presented here are understood. Some examples would include offsetting elements of the system such as passages, modifying shapes such as round or oblong profiles, changing sealing arrangements from o-rings to diaphragms or vice versa. In some cases such as in the case of offsetting passages, these may result in the need to augment or modify certain formulas provided herein to bring them in line with the modified configuration. These changes, however, would be obvious to one knowledgable in the field once they have read and understood the description provided herein and, therefore, should be considered an extension of the art revealed within this description.

It is assumed in this discussion that the design goal is a valve that can be removably fitted into a ferrule. If the designer wishes to install the valve body permanently into the vessel or conduit, the value of the relationships described herein are not lost since they can still be used to achieve the same goal of providing a valve capable of freely draining from a port installed in a configuration that is inclined from a horizontal plane.

It is one of the purposes of this invention to provide means of assuring that when the embodiment of the valve is installed in a ferrule of a vessel or conduit, the lowest point of the valve's orifice 16 will be above the down-directed drain opening 33 (the drain opening being a free-draining exit from the valve located beyond the rear-most bottom margin of the ferrule where a drain would no longer be restricted by being within the geometric confines of the ferrule) and that these two will be connected by a drainage trough within the internal cavity of the valve, trough having a bottom profile from the orifice opening to the opening of the drain opening that continuously declines at an angle greater than the angle of inclination of the axis of the ferrule's internal bore when the valve is installed in the ferrule and that inclines to the sides and to the rear from the drain opening 33. Whether or not free drainage through a flush-mounting (with the internal wall of the vessel or conduit) or penetrating (into the process, beyond the internal wall of the vessel or conduit) valve is achievable when mounted within the fixed geometry of an existing ferrule depends on three characteristics of the ferrule (as installed in the vessel or conduit). These characteristics will be discussed with reference to FIG. 2e.

Referring specifically to FIG. 2e, ferrule 2 has an internal bore 3 with three characteristic features:

1) a diameter Df of internal bore 3;
2) an angle Aa of the axis of internal bore 3 measured relative to a horizontal plane, with an inclined bore 3 have a positive angular value, a declining bore having a negative value and the value of Aa for a horizontal bore being "0".
3) Lf, the actual length of the bottom margin 56 of ferrule 2, measured from a point (Pr) formed by the bottom rear-most margin 8 of bore 3 forward to the point along the bottom margin 56 where bore 3 opens into the process and is flush with the internal wall of the vessel or conduit.

The length Lf of internal bore 3 can be broken into Lfh, its horizontal component, and Div, its vertical component. Lfh can be calculated:

$$Lfh = Lf \, COS(Aa)$$

When a ferrule is inclined, the bottom rear margin at point Pr rises up like a wall and becomes the high point of a barrier to free drainage from within the ferrule. In order to get beyond that barrier it is necessary to build a drainage trough 18 in the valve that, when installed in the valve 13 will provide an inlet at the process, the orifice 16, whose lower margin 20 forms the beginning of the trough 18 and which passes above or above and to the side of the bottom rearmost margin 8 of bore 3 down to an outlet 21 beyond the confines of the ferrule, the beginning 20 of drainage trough 18 at the base of orifice 16 being above the outlet 21 of the drainage trough 18 and where the drainage trough 18 constructed within the valve body that continuously descends at an angle greater than the angle of inclination of the axis of the ferrule's internal bore 3 when the valve is installed in the ferrule. A horizontal plane can be imagined to extend forward from point Pr wherein the drainage trough 18, beginning at the lower margin 20 of orifice 16 and passing back, just over and then beyond point Pr, is always above the horizontal plane but moving closer to it as the trough descends toward Pr, passing close but still above Pr and then beyond it to a point where it is free of the ferrule and can be drained out of the system. Thus, the beginning 20 of the drainage trough 18 (which is coincident with the base of the orifice) and the drainage trough 18 all of the way back to a point just beyond point Pr must be above this imagined horizontal plane in order for the valve to freely drain process though the inclined bore 3 in ferrule 2 beyond the point Pr.

The vertical component, Div of Lf, is the diametric height lost in order to off set bore inclination. Div can be calculated anywhere along the bottom margin 56 of bore 3 by using the value of Lf at that point and the angle of inclination Aa of the internal bore 3. For a flush-mounting design, the full value of Lf would be used and the calculation would be as follows:

$$Div = Lf \, SIN(Aa)$$

In order to actually achieve free drainage, it is necessary to impart some minimum angle of declination to drainage trough 20 that is in excess of the offset to angle Aa created by the diametric loss Div. The determination of what is a sufficient positive drain angle, Ab, is dependent on the process. The amount of diametric height necessary to create Ab in drainage trough 20 at any point along the bottom margin of bore 3 can be calculated by using the value of Lf at that point and Ab. For a flush mounted valve, the full value of Lf would be used:

$$Ddv = [(Lf) COS(Aa)][TAN(Ab)]$$

When a ferrule is installed at an inclined angle, the area where its internal bore intersects with a vertical plane such as the case with a vertical internal wall of a vessel or conduit changes from being circular to being elliptical in cross section (except in some compound angle cases). The major axis of the ellipse that forms the margin of the opening of the ferrule bore into the vessel or conduit we call the vertical diametric axis or the ferrule bore diametric height, Dfv, can be calculated:

$$Dfv = (Df)/[COS(Aa)]$$

The point tangent to the upper margin of this opening is (Pt) and will be discussed later.

The diametric height, Dfv, is the vertical height of the internal diameter of the ferrule. It is the composite sum of several diametric components. Its value is important because if it is great enough relative to Lf and to Aa, a valve which will be free draining while mounted in an inclined ferrule can be constructed.

The diametric height Dfv of internal bore 3 of ferrule 2 is composed of:

Dov: Diametric height for orifice construction.

Div: Diametric height lost due to inclination of bore 3 in ferrule 2.

Ddv: Diametric height to assure channel drainage (beyond the horizontal).

Dr1: Diametric space required to make a seal on the upper outside diameter of the valve body 13 with bore 3 of ferrule 2.

Dr2: Diametric space required to make a seal on the lower outside diameter of the valve body 13 with bore 3 of ferrule 2.

Dv1: Diametric space required to form the upper margin of annular wall 17 of the valve body 13 against which a seal is formed when the upper margin of sealing tip 30 engages the upper margin of annular wall 17.

Dv2: Diametric space required to form the lower margin of annular wall 17 of the valve body 13 against which a seal is formed when the lower margin of sealing tip 30 engages the lower margin of annular wall 17.

Dw1: Diametric space required to form the outer wall at the upper margin of the valve body 13.

Dw2: Diametric space required to form the outer wall at the lower margin of the valve body 13 or some minimum wall thickness of the bottom margin of drain trough 18 in order to allow material to flow over point Pr and down to the drain opening beyond.

Ds1: Diametric space required to allow for the interstitial space between the ID of the ferrule 2 and the OD of the valve body 13 along the body's upper margin.

Ds2: Diametric space required to allow for the interstitial space between the ID of the ferrule 2 and the OD of the valve body 13 along the body's lower margin.

In order to be able to construct a free draining valve mounted in ferrule 2:

$$Dfv> \text{ or } =[(Dr1+Dr2)+(Dv1+Dv2)+(Dw1+Dw2)+(Ds1+Ds2)+Dov+Div+Ddv]$$

This equation can be solved for Dov:

$$Dov< \text{ or } Dfv-[(Dr1+Dr2)+(Dv1+Dv2)+(Dw1+Dw2)+(Ds1+Ds2)+Div+Ddv]$$

The contribution of interstitial space is usually negligible or is difficult to differentiate from the external sealing arrangement elements so it may be folded into Dr1 and Dr2, simplifying the equation to:

$$Dov< \text{ or } =Dfv-[(Dr1+Dr2)+(Dv1+Dv2)+(Dw1+Dw2)+Div+Ddv]$$

Since wall thicknesses, sealing arrangements, interstitial space and annular seal arrangements are all determined by specific process requirements, manufacturing materials and methods which may be held constant for a range of different ferrule and valve configurations, a constant C may substituted for them and the equation rewritten as:

$$Dfv> \text{ or } =(Dov+Div+Ddv+C)$$

Or:

$$Dov< \text{ or } =Dfv-[Div+Ddv+C]$$

Or:

$$Ddv< \text{ or } =Dfv-[Div+Dov+C]$$

It is important to find the optimal combination of both the orifice side and the drainage angle in order to get the best drainage from the system.

In order to determine if it is possible to build a valve that will drain from positions within the process or from positions within the ferrule, an effective internal bore length, Lfe can be substituted into the equations for Lf. Lfe is the measured length along the bottom margin 56 of bore 3 from Pr to the point that would be coaxial with a vertical axis passing through the point 20 selected for the bottom margin of the opening of the orifice 16 into drainage trough 18. A penetrating valve design has the effect of lengthening the ferrule bore length. A longer inclined ferrule bore length results in larger values of Div and Ddv in order to maintain the steady drop over a longer effective ferrule length. This, in turn, results in less residual diametric height for the sampling orifice as well as other structural elements of the valve. If the diameter Df of bore 3 is too small, the angle Aa too steep or the length of penetration too great, all of the diametric height available in a particular ferrule installation may not be enough to compensate for the values of Div and Ddv as well as other valve diametric components. In this case it would not be possible to build a free draining valve.

For penetrating or flush-mounting valve designs, when a horizontal plane through Pr is also coplanar with Pt or when this plane passes above Pt, no free draining valve may be constructed. It is always necessary with penetrating or flush mounting designs that at least the lower margin of drainage trough 18 pass under point Pt with sufficient vertical space between the two such that the construction of the valve structural components necessary above the trough can be accomplished and yet still allow some vertical height so that flow can be achieved down the trough, past Pt.

For a system (valve and ferrule) which includes a valve with an orifice formed within the confines of the ferrule, the position of Pt is not relevant since flow can move the ferrule to and through the orifice (assuming the level of fluid in the vessel or conduit is also above the level of the orifice). In the situations where the orifice is within the ferrule bore, the new Pt is the point that is the upper margin of the ferrule bore located in a vertical plane that also passes through the lower margin of orifice 16. In fact, Pt can always be defined as the point that is the upper margin of the ferrule bore located in a vertical plane that also passes through the lower margin of orifice 16 and, in the construction of the valve, it is merely necessary that the trough originating at the base of orifice 16 descend at some angle while installed in the ferrule but still pass above point Pr or above and to the side of Pr on its.

In some large vessels equipped with relatively long steeply angled small diameter ferrules, it is not even possible to construct flush-mounting valve arrangements. In these cases the best that can be accomplished is to draw the position of the orifice back up into the ferrule internal bore to a point where there is sufficient diametric height to accommodate all of the necessary valve structural elements, including a sufficiently large orifice and a steep enough slope for the drainage trough. This situation is less than optimal since positioning the orifice up inside a ferrule places it in a "quiet" zone which will tent to stray in character from the more highly mixed body proper of the process.

Referring in detail to FIG. 1a, a vessel 53 to which the instant apparatus A will be attached is shown. It should be appreciated that the instant invention can be attached to a vessel with a static charge or to a conduit with a static or movable charge. Because this vessel itself of FIG. 1a is not a part of the instant invention, it is shown in dotted lines. As will be discussed below, this apparatus A can be mounted on the top, side or bottom of the vessel or conduit.

The vessel 53 has a ferrule 1 on the side thereof. Conventional ferrules 1 have a 25 mm internal diameter, for example. A main body 10 of the instant apparatus A has been designed to have an outer diameter generally equal to or slightly less than a standard ferrule diameter. While this 25 mm dimension has been given, it should be recognized that it is merely necessary to have the outer diameter of the body 10 of the instant apparatus A slightly less than the inner diameter of any existing size ferrule. The instant apparatus A of any size can therefore be easily retrofit to existing vessels or conduits with ports of any size. Of course, the instant apparatus can also be assembled to newly manufactured vessels or conduits.

The necessary equipment for either charging a sample to the vessel or conduit 53 or removing a sample from the vessel or conduit 53 is provided through body 10 of the instant apparatus. Therefore, it is not necessary to alter existing equipment when using the instant invention. This arrangement provides for easy retrofit with standard designed vessels or conduits.

Figure 2:
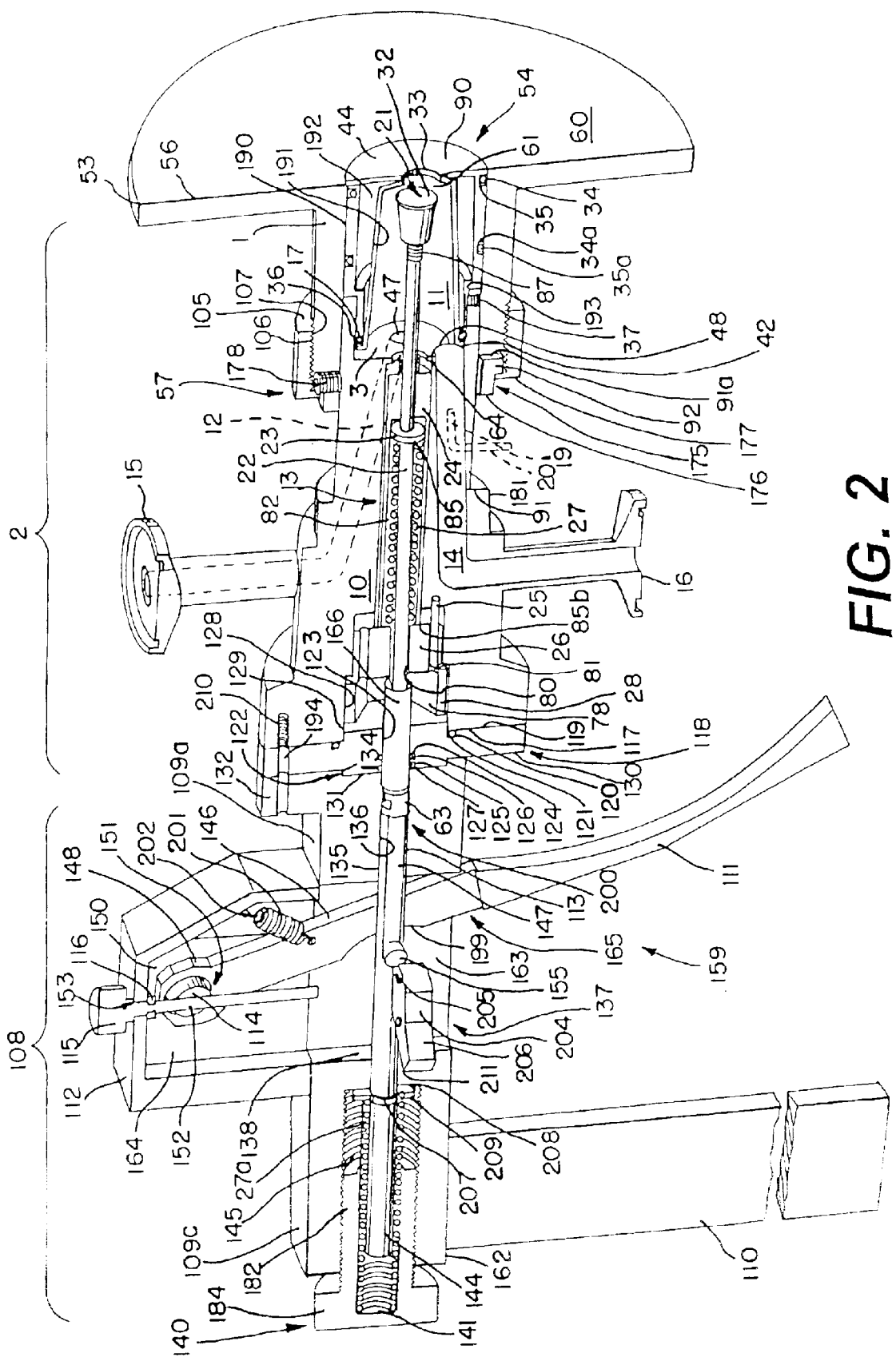
FIG. 2 is a side, sectional view of the valve and end plate with the manual trigger actuator attached.

Turning now to FIG. 2, the instant apparatus A will be described in more detail. A main sample subassembly 2 is shown connected to back end plate 118 and a manual trigger actuator mechanism subassembly 108. The main bodies of both of these subassemblies can be machined from a single piece of metal (plastic or other material) thereby providing a single, one-piece, unitary structure. By making each of these elements a single piece, the need for several additional junctions can be eliminated with the instant apparatus. Each such junction would represent a potential point for contamination, misalignment or malfunction. However, due to the unique sealing arrangements and overall design of the main sample subassembly and the trigger mechanism subassembly of the instant invention, it is not mandatory to use subassemblies machined from single pieces of metal or other material. These subassemblies can, for example, be permanently affixed (welded, glued, etc.) into single units functioning essentially as single pieces.

The main sample subassembly 2 comprises a body 10 with an internal cavity 3. This cavity 3 includes a sample cavity 11 and a central bore 13 which will be discussed in more detail below.

FIG. 3 shows a control means 4 connected to the apparatus A of the instant invention. This means can be a programmable logic controller, computer operated controller or the like. A part of the control means includes a means for detecting 4a. The operation of this control means 4 and the means for detecting 4a will be described in more detail below.

A supply means 50 is provided for supplying at least one of steam, air and wash medium to the apparatus. This supply means 50 helps maintain an aseptic environment. In some situations, steam alone is sufficient for cleansing the system. In other uses, it is necessary to use pure dry air or a wash medium. Moreover, any combination of these materials can be used. The wash medium can include detergents, alcohol, an alkaline rinse, acid rinse or other wash material. It should be evident that many different arrangements can be used for cleaning and/or sterilizing the instant invention.

The supply means 50 of the instant invention includes a steam feed valve block 5, a pure dry air valve block 6 and a wash medium valve block 7. The steam feed valve block 5 includes a steam source 66 connected to a diaphragm pneumatic valve 67. Also connected to this valve 67 through an electromagnetic valve 69 is a pressurized air source 68. It should be noted that any suitable type of automatic or manual valves 67 and 69 can be used in the instant invention or that these two valves can be combined into a single unit.

The pressurized pure dry air valve block 6 includes a pure dry air source 70. This pressurized pure dry air source 70 is connected to a diaphragm pneumatic valve 71. Also connected to this valve 71 through an electromagnetic valve 72 is a source of pressurized air 73. Similarly to valves 67 and 69, it should be understood that any type of valve can be used for the valves 71, 72. Also, a single unit could replace these two valves 71, 72.

The wash medium valve block 7 includes a supply of wash medium 74. As noted above, this wash medium can be a detergent wash, an alkaline wash, an acid wash, an alcohol wash or any suitable cleansing arrangement. The supply for wash medium 74 is connected to a diaphragm pneumatic valve 75. Also connected to this valve 75 through an electromagnetic valve 76 is a source of pressurized air 77. Again, similarly to valve 67, 69, 71 and 72, any suitable valve or a single unit can be used for these valves 75 and 76.

The electromagnetic valves 69, 72 and 76 are indicated as being connected to the control means 4. It should be noted that the diaphragm pneumatic valves 67, 71 and 75 are also connected to the control means 4. It is merely necessary for the control means 4 to control supply of steam, pure dry air and/or wash medium to the inlet passage 12. Each of these mediums is connected to the inlet passage 12 through the respective valves 67, 71 and 75. Moreover, while three valve blocks 5, 6 and 7 are shown, any of these can be omitted or additional valve blocks could be used as needed. Also, valves 69, 72 and 76 can be combined into a single valve.

The inlet passage 12 is shown as being continuous from the main sample subassembly 2 to the supply means 50. As noted above, this main sample subassembly can be machined from a single block. Appropriate tubing, piping or other connectors can be used to connect the inlet passage 12 bored within the main sample subassembly 2 to the supply means 50. A tri-clamp connection 15 connects this tubing or piping to the inlet passage within the main sample subassembly. It should be noted that it is usually possible to perform all of the functions normally expected of the above described inlet port through either the sampling orifice (33, described later) in combination with the drain passage 14. For this reason in many cases it may be possible to eliminate the inlet port.

A drain passage 14 is also provided in the instant invention. This drain passage can be bored within the main sample subassembly 2 or can be piping connected to a downstream means for collecting a sample 51 and means for collecting drain 52. These means 51 and 52 will be discussed in more detail below. Similarly to the connection for the inlet passage at 15, the drain passage 14 has connection 16. Rather than using a tri-clamp at the connections 15 and 16, any suitable connection arrangement can be made.

Both the inlet passage 12 and drain passage 14 are connected to the interior sample cavity 11 of body 10. This body 10 not only includes sample cavity 11 but the central bore 13 which together form the above-noted internal cavity 3.

Internal Portion of Valve

Figure 2A:
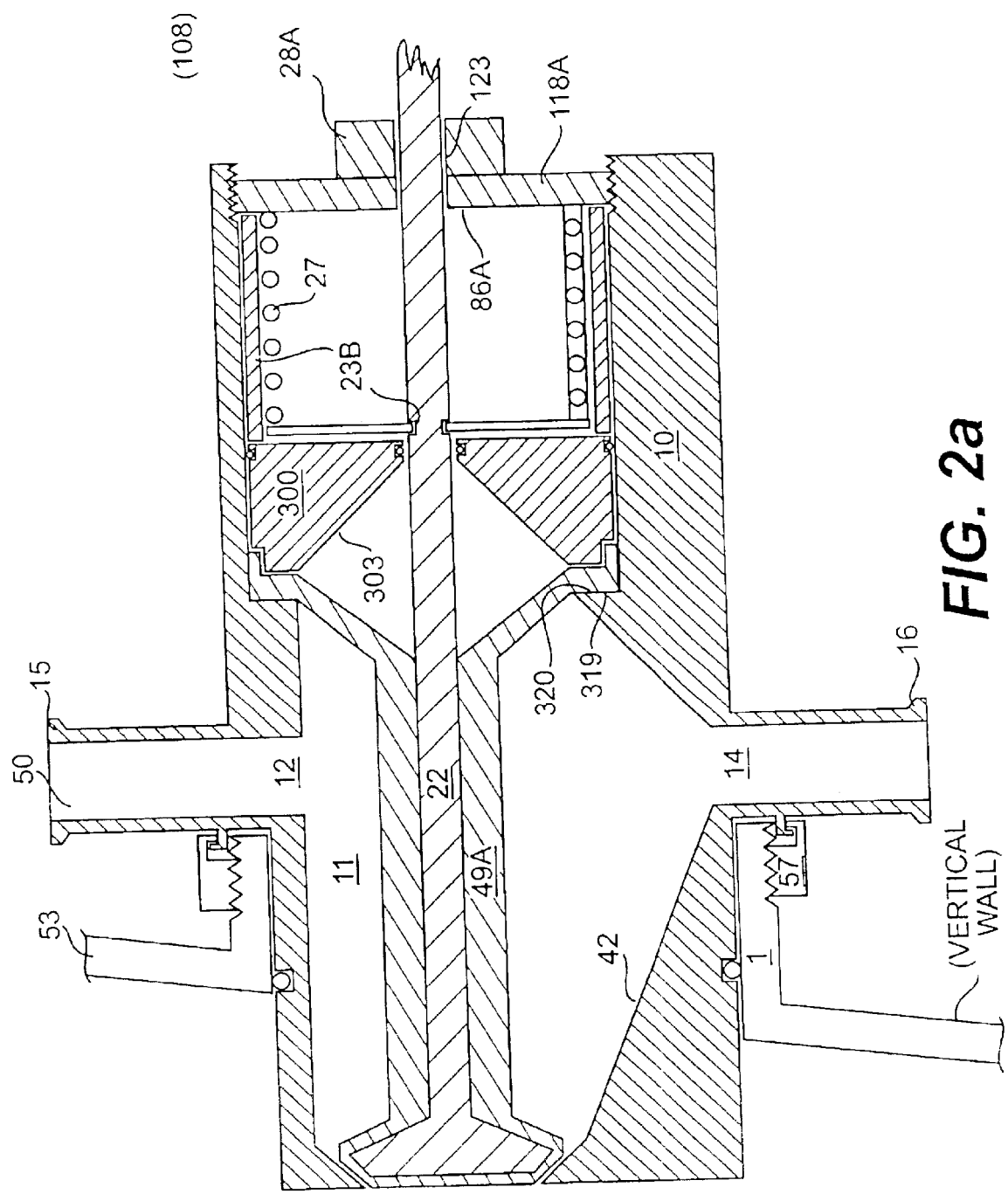
FIG. 2a is a cross section of a valve assembly (made of insulating material) without an actuator in an inclined ferrule, penetrating into the body of a vessel or conduit.

From the rear of sample valve 2, the valve operating rod 22 extends forward through the central bore 123A of the a spring backstop 118A which will be discussed later and into the central bore 13 of body 10 as seen in FIG. 2A. Within central bore 13, rod 22 extends forward through diaphragm backstop 300. While the combination spring backstop 118A and diaphragm backstop 300 are shown, it should be appreciated that any appropriate arrangement can be used for mounting the valve operating rod 22 in the body 10. By using such parts 118A and 300, however, assembly and disassembly of the sample subassembly 2 can be easily carried out.

Extending between seat 86A of the spring backstop 118A the valve operating rod detent 23 is a spring 27. This spring 27, shown in FIG. 2a, will urge the operating rod 22 away from the actuating means located to the rear. This will cause blunt sealing tip 32 of diaphragm 49A to close the orifice 33 as will be discussed in more detail below. By urging the tip 32 in this direction, the instant apparatus will automatically close orifice 33 upon a power failure. Thus, safe operation of the instant apparatus can be ensured.

Figure 2B:
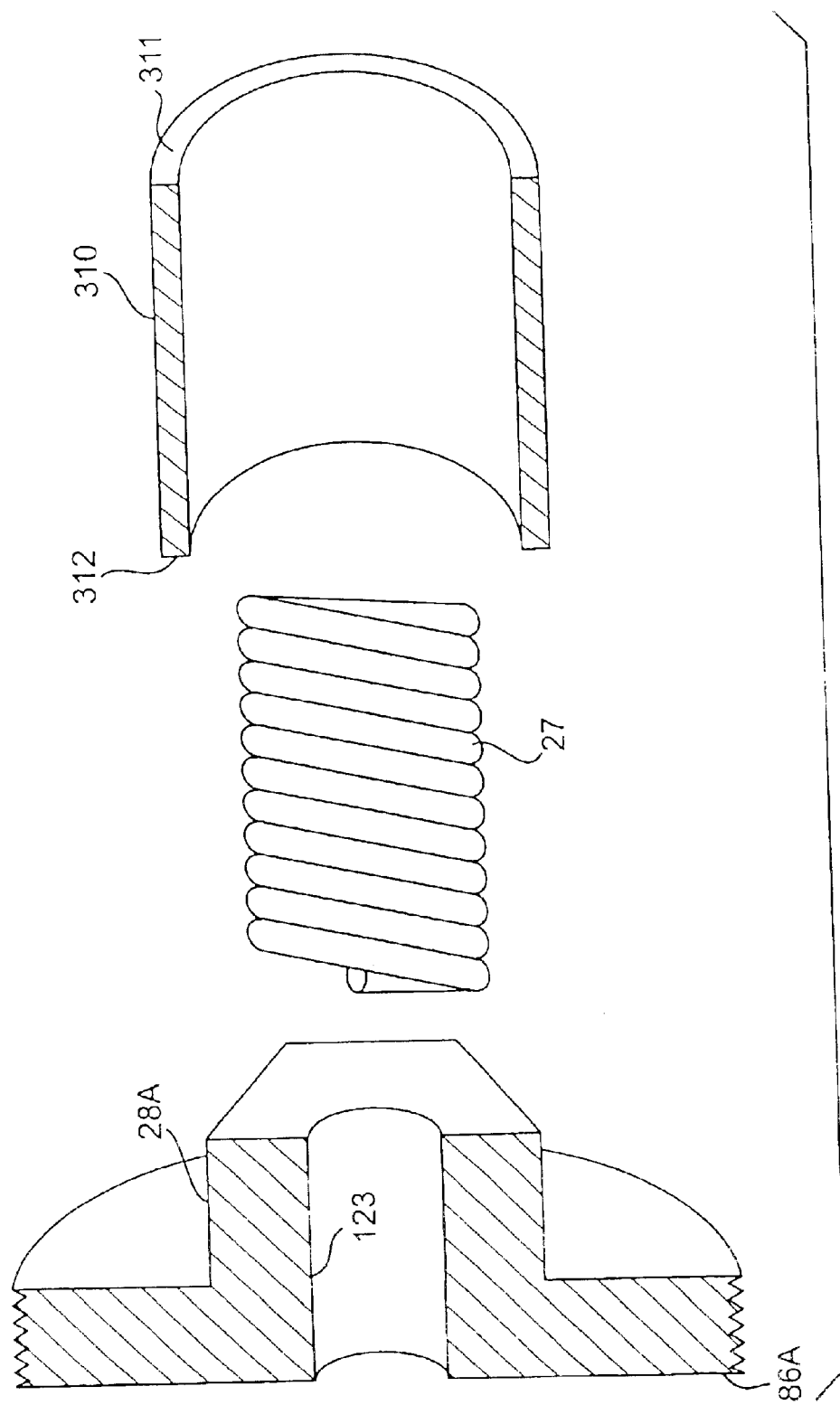
FIG. 2b is a cross section of the spring backstop, spring sleeve and full view of the spring.

Turning to FIG. 2b, the spring backstop 118A is shown along with its central bore 123A and spring seat 86A. Also shown in this figure is a hexagonal rearward extension, rear hex 28A, with the central bore 123A of spring backstop 118A also extending through it. Valve operating rod 22 will, therefore, also extend through this bore when it is inserted through 118A. Also shown is spring sleeve 310, its rear face 311 and forward face 312.

Figure 2C:
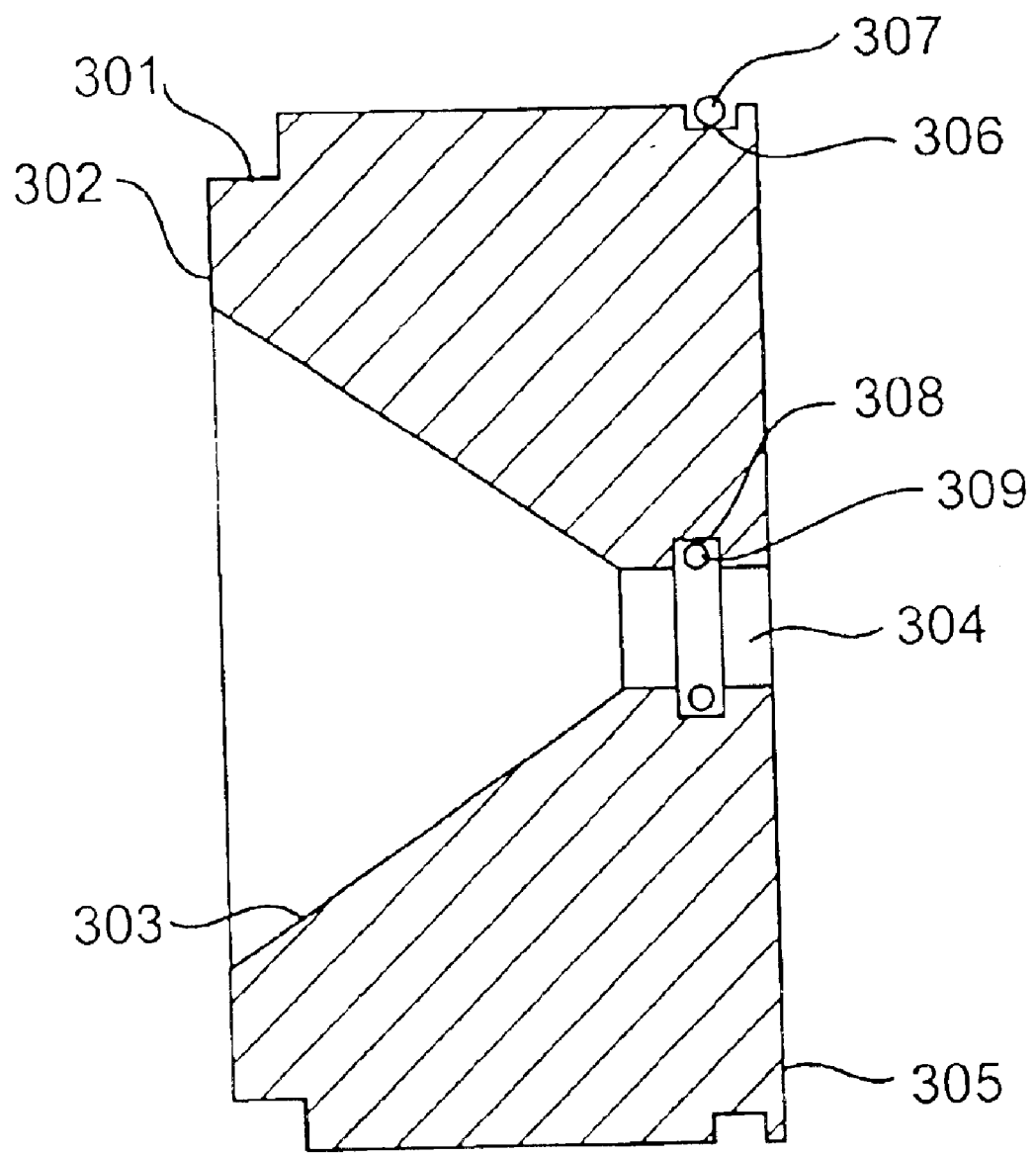
FIG. 2c is a cross section of the diaphragm backstop.

In FIG. 2c, diaphragm backstop 300 is shown with its parts, diaphragm detent 301, backstop forward face 302, pressure seat 303, central bore 304, backstop rear face 305, body seal o-ring groove 306, body seal o-ring 307, rod seal o-ring groove 308 and rod seal o-ring 309.

Figure 2D:
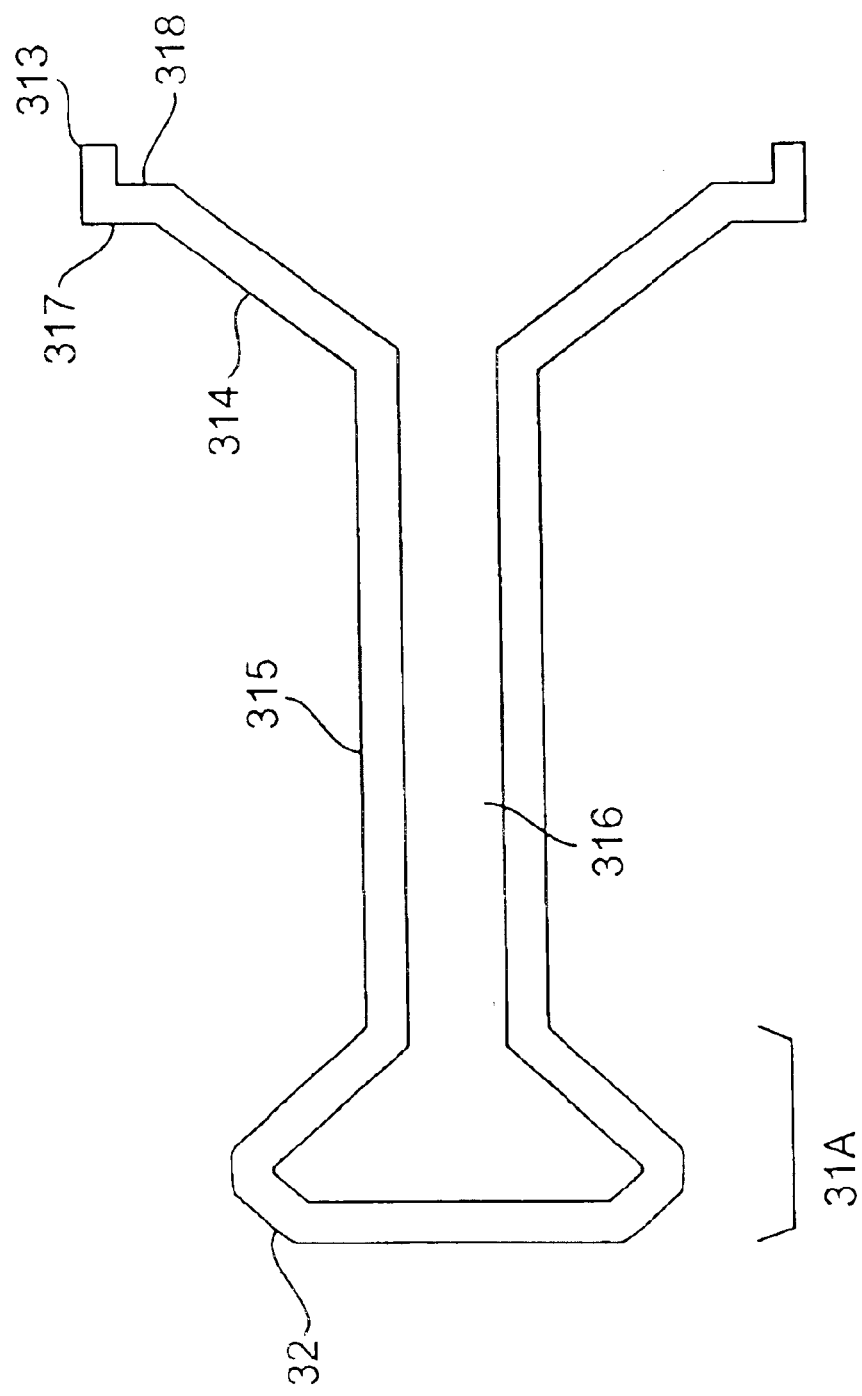
FIG. 2d is a cross section of a diaphragm with a conical base.
Figure 2F:
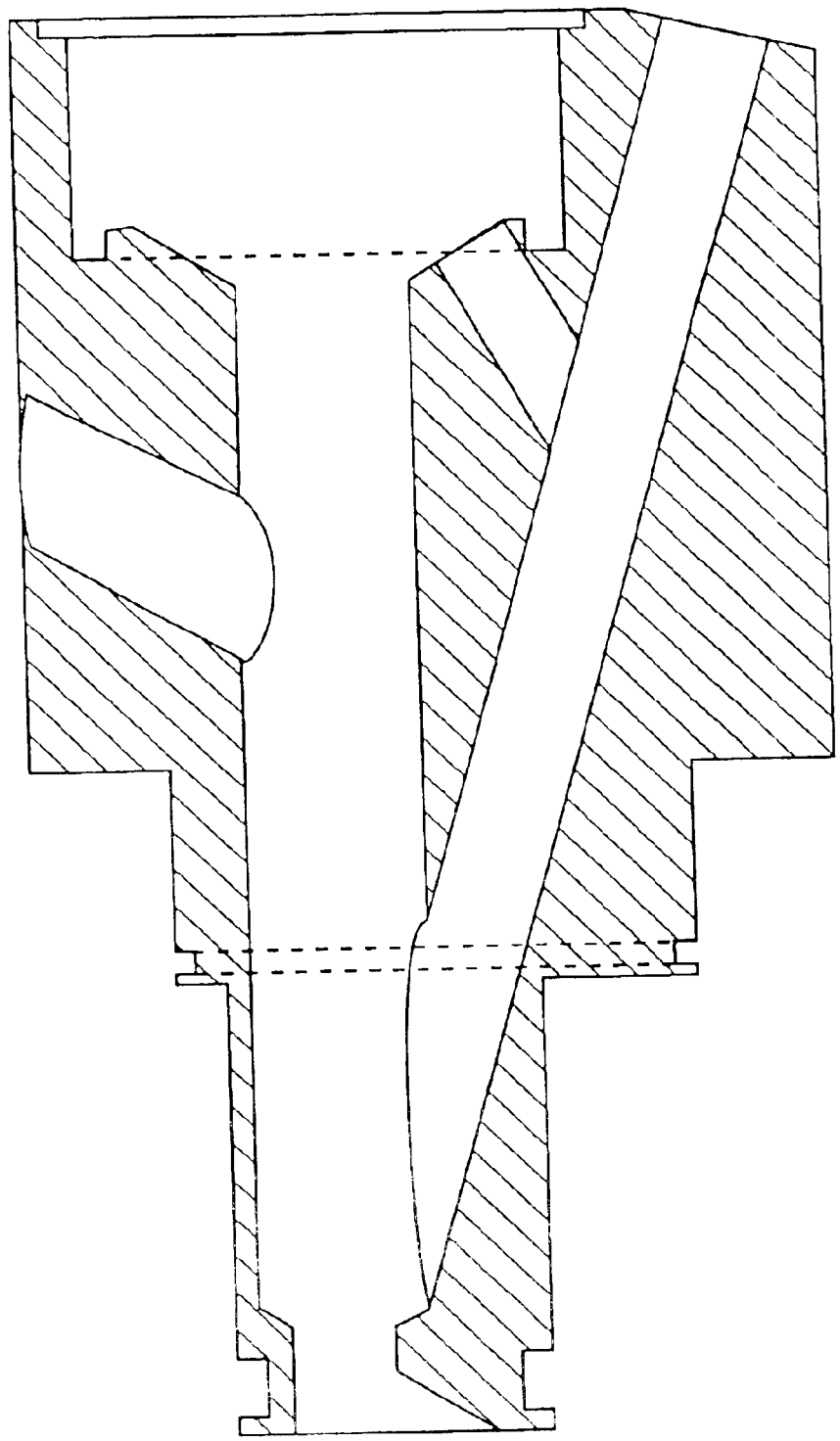
FIG. 2f is a side cross sectional view of a portion of the valve assembly without an interior portion of the valve housing above the drain passage removed.
Figure 29:
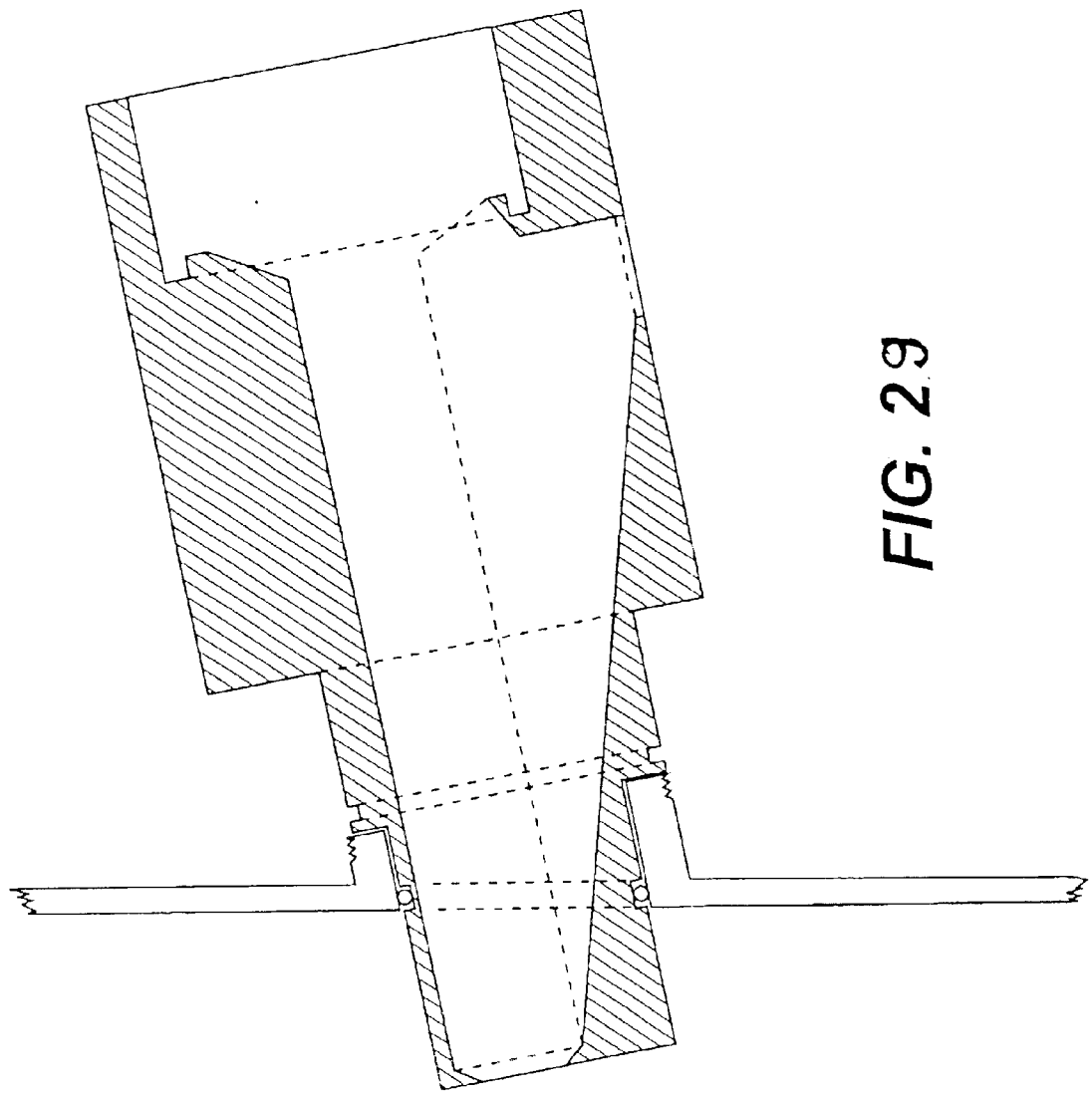
Figure 4:
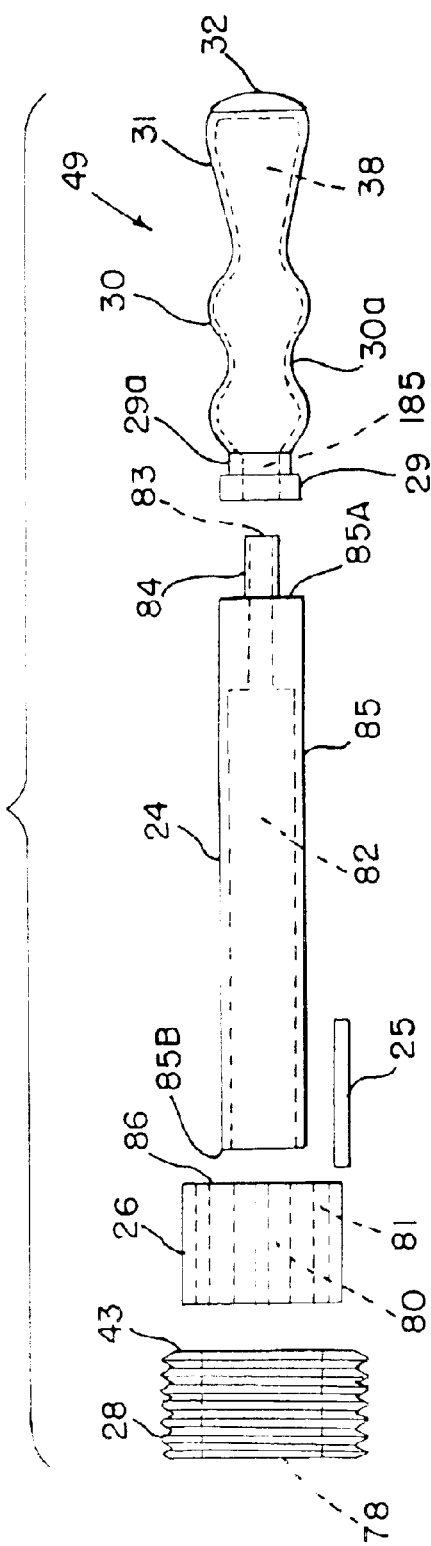
FIG. 4 is an exploded view of some of the various parts associated with the valve.
Figure 7:
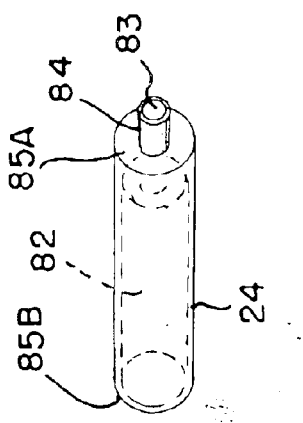
FIG. 7 is a perspective end view of the bushing shown in FIG. 4.
Figure 6:
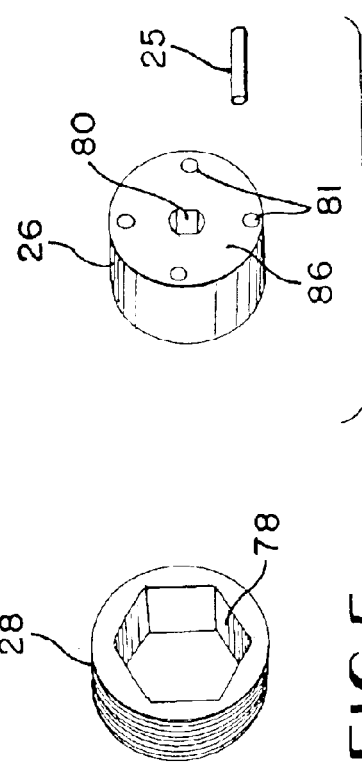
FIG. 6 is a perspective end view of the non-rotating spacer and stabilizer pin shown in FIG. 4.
Figure 5:
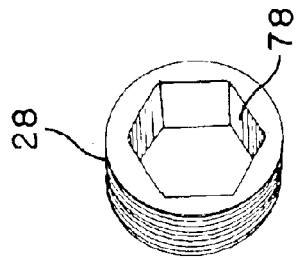
FIG. 5 is a perspective end view of the rear valve operating nut shown in FIG. 4.

FIG. 2d shows diaphragm 49A with its parts, blunt sealing tip 32, shank 315, flexing cone 314, front base seal 317, back base seal 318, annular lip 313 and rod cavity 316.

FIG. 2a illustrates the assembled sampling valve. The internal parts are assembled into the valve from the rear starting forward most with the diaphragm and moving back. Assembly is as follows: Diaphragm 49A and valve operating rod 22, which are shown together, may be assembled by slipping diaphragm 49A onto rod 22 from the rear of the diaphragm. It should be noted that the whole diaphragm, only a portion or none of the diaphragm might be molded onto rod 22. If the two are not molded together, the rod 22 may be fitted into the diaphragm through the opening to its cavity 316 found in the center of the flexing cone base.

Once assembled, the diaphragm/rod combination can be slipped forward through the back of body 10 until front base seal 317 engages the real annular diaphragm mating face 319. Diaphragm backstop 300 is slipped over the rear portion of rod 22 until its backstop forward face 302 and diaphragm detent 301 engage back base seal 318 and annular slip 313 of diaphragm 49A. Next, valve operating rod detent 23 may be slipped onto the rod and snapped into the groove on rod 22. Next, spring 27 can be slipped over rod 22 until its forward end engages the rear wall of spring detent 23. Spring sleeve 310 can be slipped around spring 27 and into the rear portion of central bore 13 of internal cavity 3 of body 10 until the forward face 312 engages backstop rear face 305. Lastly, spring backstop 118A can be slipped over the rear portion of rod 22 until its external threads engage the internal threads of body 10. By applying a hex wrench to rear hex 28A and tightening it into body 10, its forward face (spring seat 86A) will urge spring sleeve forward against the backstop rear face 305 which in turn will press up against the back base seal 318 and annular lip 313, causing front base seal 317 of diaphragm 49 to seal against the annular sealing surface of body 10. The tightening of spring backstop 118A also causes spring 27 to be compressed against the spring detent on rod 22, thereby urging the shaft's tip and the diaphragm sealing tip 32 against the annular sealing surface about orifice 33.

When valve operating rod 22 is retracted, blunt sealing tip 32 will be withdrawn from orifice 33, allowing material to flow into sample cavity 11 and down and out drain 14. When the actuator is inactivated (whether a manual or automated device), the compressed spring 27 acting against detent 23 will urge blunt sealing tip 32 forward until it again the sealing surface about orifice 33. The blunt sealing tip 32 of diaphragm 49A tends to form a good seal, helping to minimize deadspace at orifice 33. Of course this blunt sealing tip can be configured in many ways. It is merely necessary that an appropriate seal be formed with the orifice.

Spring detent 23A consists actually of a retainer ring fitted into a retainer ring slot 23B along rod 22. A washer can be added to form a more uniform mating surface with the spring.

Spring detent 23 can, of course, be an integral part of operating rod 22 but if operating rod 22 is machined out of a solid bar stock rod, making the spring detent an integral part would simply mean more work since it would require starting with thicker bar stock. In some cases, however, making this as one piece may be advantageous.

Alignment of the valve internal components can be seen. To the rear, alignment for the valve operating rod is provided by the bearing surfaces of central bore 123 in spring backstop 118A and forward, alignment is provided by the bearing surfaces about o-ring grove 308 of diaphragm backstop 300.

FIGS. 2a and 2c both show the pressure seat 303. The space in front of this surface provides room for the conical portion 314 of the diaphragm 49A to flex into. It also serves as a support structure in case the diaphragm is subjected to high pressures. The diaphragm may also be strengthened by the incorporation of fibers during its construction.

While a diaphragm with a large sealing tip, a reduced diameter shank and large base is shown, it could be constructed in many other ways. It is only important that there be associated with it an effective sealing tip and a shaft and base portions that allows the tip to be reciprocally opened and closed without exposing the process or sampled material to the mechanical components of the valve.

The use of a diaphragm 49 with conical flexing base 314 and blind bulb end 31A has several benefits. First, all of the moving mechanical parts (such as the valve operating rod 22A and other components associated with central bore 13) are removed from the sample in sample cavity 11. The diaphragm 49A with its conical flexing base 314 are made from a biocompatible rubber, plastic or metal material with thermal and chemical tolerant properties. Furthermore, these components are flexible and have a wide range of motion. This great range of motion allows the apparatus to achieve a flush (or penetrating) mounting condition on a vessel or conduit, even when retrofit to an existing design.

Further, this design allows the blunt sealing tip 32 to be withdrawn from the sampling orifice 33 over a great distance. This facet allows the apparatus to provide minimal sample size bias for samples with particles up to at least six mm size in this particular configuration.

FIGS. 4, 5, 6 and 7 show portions of another valve rod and diaphragm arrangement. A detailed discussion of these Figures can be found in parent application Ser. No. 08/613,586 filed Mar. 12, 1996, the entire contents of which, as noted above, are incorporated herein by reference.

In FIGS. 8, 9 and 10, the valve operating rod 22 and valve operating rod cap 21 are shown. One end of this valve rod 22 has a thick annular groove cut around it, resulting in a short section of narrow shaft, the connector shaft 170. Behind that is the remaining short section of larger diameter shaft, the connector cap 169. On the other end of rod 22 are a set of male threads 87 to mate with the female threads 88 in cap 21. These permit rod 22 to be screwed into: cap 21. Of course, other connection arrangements can be made.

A discussion of the connection of the actuators and their connection to the operating rod will be discussed below.

Blunt sealing tip 32 will assuredly seal orifice 33 and not deform and protrude through the orifice 33, because the tip 32 is backed by a metal cap which gives solid support. Also, this cap 21 will prevent tip 32 from sticking to the area around the orifice 33 when the operating rod 22 is retracted.
Endcap The orifice 33 is provided in the body 10 as seen in FIG. 2a. This arrangement is made possible by the modification of the internal components and the incorporation of the cap into the valve body. This has allowed the elimination of the set screws previously required to hold the endcap 44 in place. It has also allowed the elimination of alignment concerns, o-ring 17 and groove 36 as well as the seam associated with the o-ring and groove. This has also allowed the development of a smooth, crevice-free internal cavity which is capable of providing better drainage from sample valves installed in ferrules with higher angles of inclination.

In FIG. 11 of the previous embodiment shows the double walled nature of cap 44. The cap 44 has resulting features and benefits including properties. In this later embodiment where cap 44 is an integral part of body 10, the double wall nature of cap 44 along with the insulating properties can also be incorporated into body 10. Besides double walled, insulating properties can also be achieved having a single wall if that wall is coated, inside and/or outside, with an insulating material. Lastly, insulating properties can be conferred onto a design by fabricating the design itself out of materials with highly insulating properties.

By appropriate selection of materials, body 10 can not only exhibit insulating thermal properties but also electrical as well. Key among the benefits of these insulating properties is the ability to protrude the sampling orifice into the body of a process that is heat labile. This allows the placement of a heat resterilizable sampling tip to be placed in a heat labile process in an area adjacent to where in-situ measurements are being taken, significantly increasing the value of the sampled material and its relevance to the development effective process monitoring and control.

To improve drainage from orifice 33 down and out of the sample cavity 11, the inner walls of cap 44 in the previous embodiment were inclined as could be seen in FIG. 11. These inner walls could be parallel to the outer walls of the cap 44 if so desired but the alternative inclined arrangement would not be adversely affected if the apparatus A were used in an inclined ferrule.

As will be discussed later, the forward end of the valve, including tip 32, can be extended beyond the inner wall 56, where a stagnation layer forms to a greater or lesser degree, into the vessel or conduit interior. By moving the sampling orifice 33 into the body of the fluid, interference from stagnating material along the margins is reduced, increasing the level of quality of representation that the sample has of the bulk of the process. The character of the sample will also correlate better with measurements taken from sensors since their sensing elements are also positioned away from the wall in the bulk of the process. In many cases it is not sufficient to have only the ability to withdrawal a sample from deep within a tank, it is also important that the process be thermal or electrically protected. The most recent embodiment of the valve may include an insulated body in order to minimize any adverse effects that might occur as a result of any thermal or electrical treatments that may be done to the valve interior between sampling events. These insulating properties will significantly improve the ability to correlate in-situ sensor data with the actual conditions at those points within the body of process by virtue of the current invention being capable of being installed with its sampling orifice adjacent to the sensors without adversely affecting the process.

Mounting to a Slanted Wall

In the arrangement shown in FIG. 12, the wall 56 of the vessel or conduit is shown as being slanted. It should be appreciated that many different configurations for the vessel are also possible. The forward end of the body 10 and/or cap 44 can be appropriately sloped in order to mate with the interior face of the wall 56. In so doing it is important to assure that some seal such as an o-ring seal is formed between body 10 or cap 44 and the inside wall of the ferrule adjacent to wall 56.

Coupler

Figure 13A:
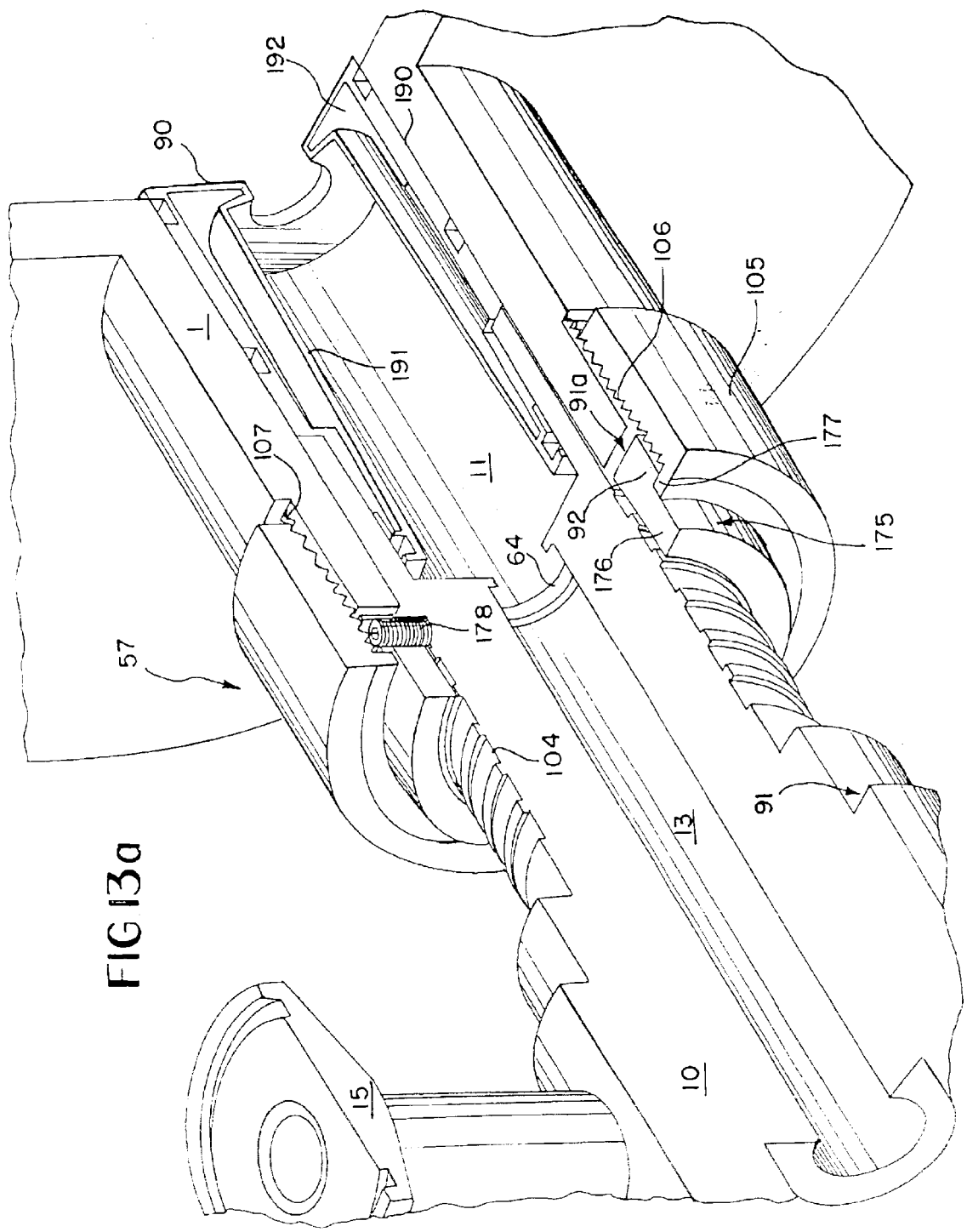
FIG. 13a is a perspective, orthogonal side, sectional view of an adjustable coupling means

In FIG. 13A, a means 57 is shown for coupling body 10 to ferrule 1. This special screw-type connection can be repositioned along a length of body 10. This coupler, alone, allows body 10 to be fitted effectively, in a flush-mounting condition or otherwise, to ferrules having a variety of different lengths.

Around body 10 and extending for a distance forward from front side 91 are a series of evenly spaced, uniform circumferential positioning grooves 104. Movably positioned in front of front wall 91 of body 10 and around body 10 is a short cylindrical positioning collar 175. Positioning collar 175 has a retainer flange 92 flush with its front wall 91a. Extending through flange 92 in radial fashion are a set of threaded through holes with set screws 178. These are evenly spaced around its circumference. Leading away to the rear from the flange is a smaller diameter shoulder 176. Positioning collar 175 has a uniform cylindrical inside surface which allows it to move smoothly back and forth on body 10 when set screws 178 have been sufficiently loosened. Coupling nut 105, consisting of an internally threaded cylindrical section 106 ending in a short inner annular lip 177, is positioned around body 10, behind positioning collar 175. This inner annular lip is of a smaller diameter then the outer diameter of flange 92 but greater than that of shoulder 176. Thus, coupling nut 105 can be slipped forward over shoulder 176 so that the forward wall of its inner annular lip 177 can engage the rear wall of flange 92 but preventing it from ever passing around flange 92. The diameter of its inner threads are only slightly greater then the outside diameter of flange 92. The length of set screws 178 in positioning collar 175 have been selected so that their heads will be flush with the outer surface of flange 92 only when they are threaded firmly down into one of the positioning grooves 104 on body 110. The forward threaded portion 106 of coupling nut 105, therefore, cannot be slipped forward over set screws 178 and be made to engage with the external threads 107 of ferrule 1 until set screws 178 are all tightened down firmly onto body 10. Coupling nut 105 can then be tightened onto threads 107 of ferrule 1 until front wall 91a of positioning collar 175 engages the rear wall of ferrule 1. With coupling nut 105 tightly fixed to ferrule 1 and covering set screws 178 which are tightened into a groove 104, and because inner annular lip 177 of coupling nut 105 can not slip by retainer flange 92, main sample subassembly 2 is firmly but removably fixed to ferrule 1. Any other subassemblies attached to subassembly 2 will, therefore, also be firmly but removable attached to ferrule 1.

With coupling nut 105 pulled back and set screws 178 sufficiently loosened, position collar 175 can be repositioned along body 10, allowing main sample subassembly 2 to be adjusted to fit different length ferrules or, in a given ferrule, to change its interface with the process from one of flush mounting to one of penetration.

Figure 13B:
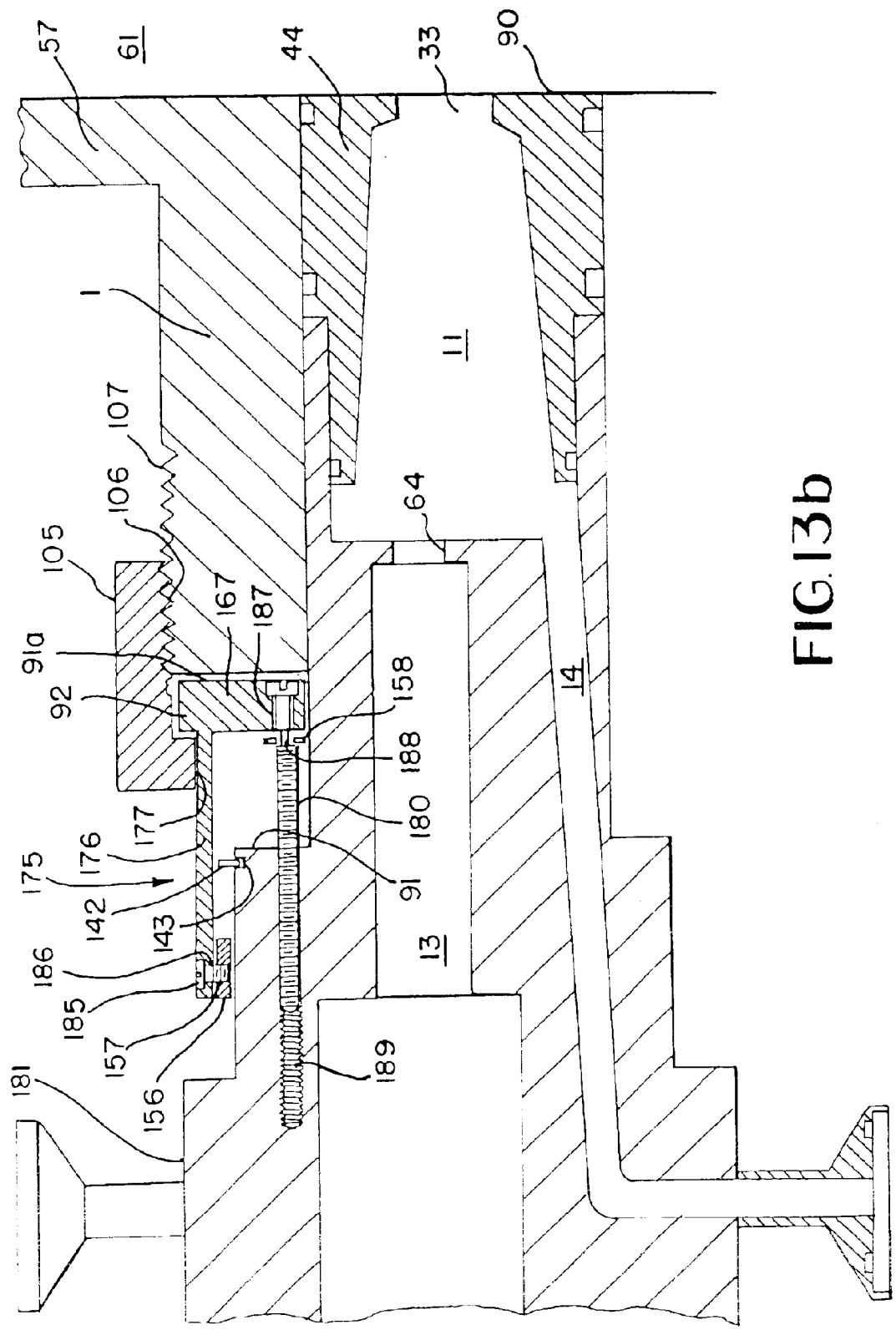
FIG. 13b is a side, sectional view of an alternative adjustable coupling means.

Another means, illustrated in FIG. 13b, though a little more complex and expensive, will now be described. The cross section shown in FIG. 13b only has a detailed showing and reference numerals included for the upper quarter part of the cross section shown. The description follows its assembly onto body 10. First, body 10 has an annular shoulder 181 with a forward wall 91. A short cylindrical retainer sleeve 156 with a set of evenly spaced threaded holes 157 radiating outward, is slid over annular shoulder 181 of body 10 and is retained there by a retainer ring 142 held in a groove 143 in annular shoulder 181 just behind forward wall 91.

A coupling nut 105, consisting of a hollow cylindrical section with a forward internally threaded cylindrical section 106 having an inner annular lip 177 on the rear side thereof, can slide freely around the rear portion of a positioning collar 175. The positioning collar 175 consists of a long, relatively thin cylindrical sleeve or shoulder 176 extending to the rear and with a set of screw through-holes 186 located near but not at its posterior margin. Forward, the positioning collar 175 has a short, double flanged cylindrical section, the outer radiating flange is retainer flange 92 while the inner radiating flange is positioning flange 167 and the forward wall of both of these being the forward wall 91a of positioning collar 175. There are a set of longitudinal through holes 187 bored longitudinally through forward wall 91a and flange 167 adjacent to its inner annular margin. These holes 187 are fitted with countersunk coupler positioning screws 180. These coupler positioning screws 180 are held captive in flange 167 of positioning collar 175 from behind by retainer rings 158 riding in grooves 188 in the screw shafts and from the front by the screw heads which are counter sunk in the forward wall 91a of positioning collar 175.

The coupling nut 105 can be slipped onto the positioning collar 175 from behind and held from slipping off the front by the retainer flange 92. With cylindrical retainer sleeve 156 already in place on shoulder 181 of body 10, the positioning collar 175 with the coupling nut 105 already around it can be slipped around body 10 from the front. Positioning screws 180 can be threaded into the longitudinal holes 189 in the front wall 91 of body 10. When these screws 180 are threaded in holes 189 far enough, screw holes 186 of the shoulder 176 will align with the threaded holes 157 in the cylindrical retainer sleeve 156. At that point, a second set of screws 185 are fitted through holes 186 in shoulder 176 and tightened radially into threaded holes 157 in cylindrical sleeve 156. Once these screws 185 are tightened, coupling nut 105 is captured behind retainer flange 92 of positioning collar 175 on body 10. Furthermore, the position of flange 92 and forward wall 91a which engages the back wall of ferrule 1 during coupling, can be adjusted along body 10 relative to the position of orifice 33 simply by threading screws 180 in or out of holes 189 in body 10. Thus, sampling subassembly 2 can be custom fit to vessels and conduits with a variety of ferrule lengths as well as providing a means to couple the apparatus in a penetrating fashion in a ferrule of given length.

Because the forward advance of the coupling collar 175 is stopped by the engagement of the forward wall of cylindrical retainer sleeve 156 with the rear wall of retainer ring 142 before the longitudinal screws can be threaded out of their respective holes, a user cannot inadvertently disengaged the coupler 57 from the valve, a potentially dangerous event should the vessel then be pressurized.

O-rings and grooves to receive the o-rings can be added along the inside circumferential surfaces of cylindrical retainer sleeve 156 and positioning flange 167 to inhibit this region from collecting dirt.

A third method of removably attaching the main sample subassembly 2 is shown in FIG. 1b. This arrangement is even simpler than the designs shown in FIGS. 13a and 13b. Here, a helical thread 186 is provided around the circumference of the forward end of the main body 10 in front of the front side 91. This thread 186 takes the place of the positioning grooves 104. A positioning collar 175 with a rear annular lip can be threaded on thread 186. This allows for an infinite number of adjustment positions over the threaded range. The threads would not allow the positioning collar 175 to become disengaged unless the collar was threaded too far forward. Such a problem could be avoided by placing a (low profile) retainer ring at the forward end of the threads. When the positioning collar 175 was farthest forward, it would engage the retainer ring. When collar 175 was farthest back, the front wall 91a of positioning collar would be flush with the front wall of this retainer ring.

Of course, there are other methods to removable attach the main sample subassembly 2 and these means can be modified in various ways. An example would be the elimination of the grooves 104 on body 10. Though they provide a certain added safety margin, grooves 104 are not essential for the coupling means to work properly or effectively.

Back End Plate

Figure 14:
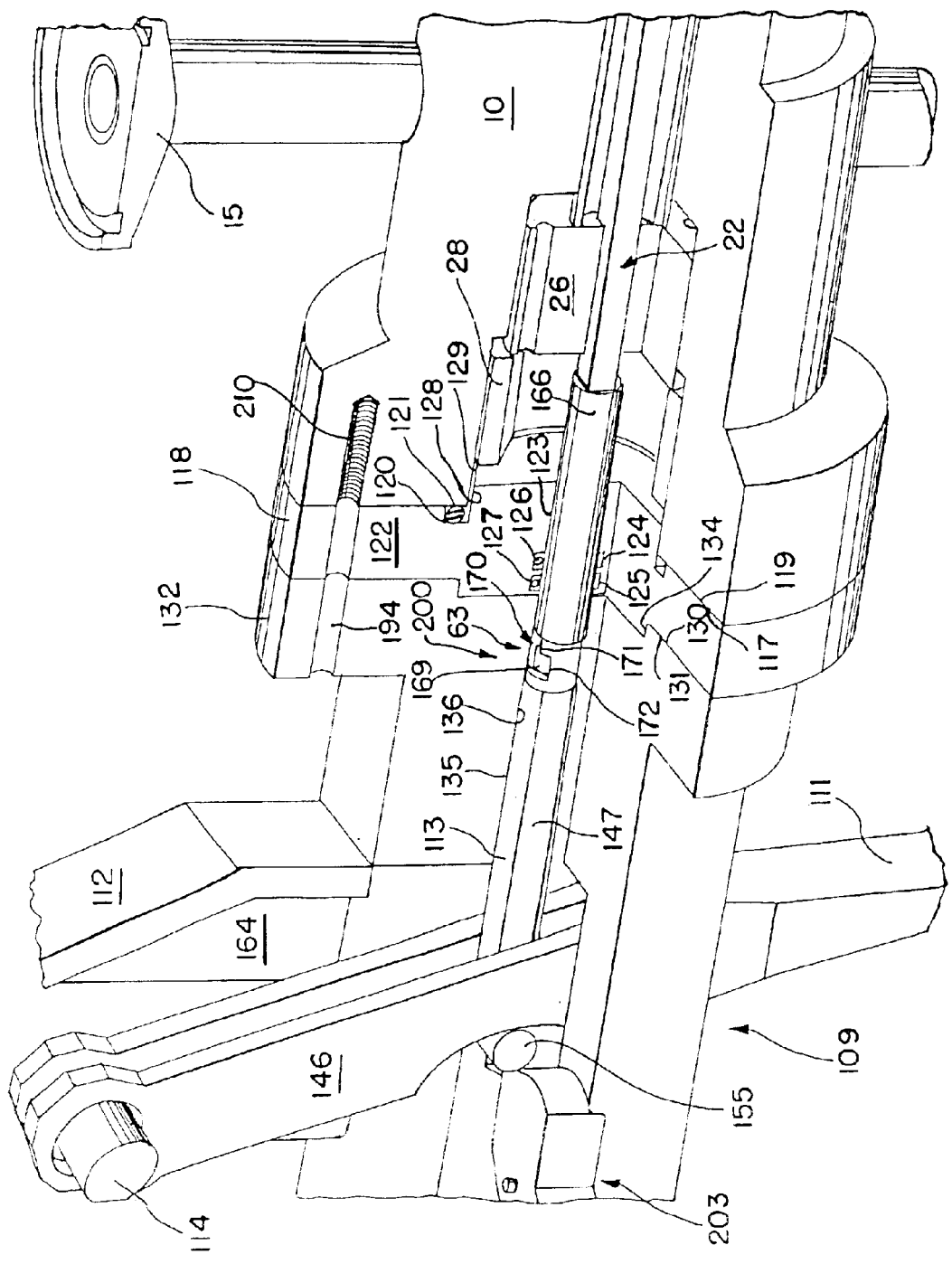
FIG. 14 is a perspective, sectional view of a backend plate in position between the valve and the manual trigger actuator assembly the means for coupling.

Engaged with the rear wall 119 of body 10 is the front wall 117 of back end plate 118 as seen in FIG. 14. This engagement creates a static annular seal between o-ring groove 120 and o-ring 121 of back end plate 118 and rear wall 119 around central bore 13. An annular section 122 with a longitudinal axis parallel and coinciding with the axis of the central bore 13 protrudes out from front 117 and rear 130 walls of back end plate 118 as seen in FIG. 14. Cut into the walls of the cylindrical bore 123 of this annular section 122 are one or more annular o-ring grooves 124 (and 125) equipped with o-rings 126 (and 127). A double o-ring arrangement is illustrated in FIG. 14. The rear cylindrical portion 166 of valve operating rod 22 extends through cylindrical bore 123. O-rings 126 (127) form a sliding seal between o-ring grooves 124 (125) and cylindrical portion 166 of valve operating rod 22. Collectively, o-rings 121 and 126 (and 127) seal the inside of the valve from the outside environment and serve as a secondary seal against leaks of the process material to the outside should diaphragm 49 fail. Likewise, they serve as secondary seals protecting the process from the outside environment. Other means of sealing the valve interior from the outside environment could also be used. For example, the seal formed at o-ring 121 between back end plate 118 and rear wall 119 of body 10 could be moved to an annular position on the alignment lip formed by the outside circumferential wall 128 of the forward protruding portion of the annular section 122 in FIG. 14 which mates with circumferential wall 129 of central bore 13. Similarly, the seal created between the cylindrical bore 123 of annular section 122 and the valve operating rod 22 could be made by placing the o-ring grooves in the operating rod. If this latter approach to sealing about rod 22 is chosen, it may be necessary to extend a portion of annular section 122 to a point closer to the back wall of spacer 26 but with a smaller outside diameter so that it fits within the hexagonal bore 78 of rear nut 28. This will allow a longer continuous surface for the o-rings in the cylindrical portion 166 of rod 22 to seal with cylindrical bore 123. One of the advantages of this arrangement is that of providing a longer alignment surface in back end plate 118 to engage operating rod 22.

Once the intent of plate 118 and its seals have been described, it should be clear to anyone familiar with the art that many other sealing arrangements could be used so long as the sealing purpose is achieved.

Assurance of alignment of back end plate 118 with components of the main valve body 10 and, in particular, valve operating rod 22, is achieved by mating of opposing planar surfaces of front wall 117 of back end plate 118 with rear wall 119 of body 10 as well as the close fit of the alignment lip created by the outside circumferential wall 128 of forward protruding portion of annular section 122 mating with an opposing circumferential wall 129 of central bore 13 adjacent to its intersection with the rear wall 119 of body 10. Of course, it should be understood that proper alignment could be achieved in a variety of other ways. These could include: a series of alignment pins or screws in back end plate mating with an opposing set of alignment holes in body 10 (or vice versa); threading outside circumferential wall 128 to mate with the threaded section of central bore 13 behind rear valve operating nut 28; and other arrangements of opposing alignment surfaces or walls machined to relatively fine tolerances.

Back end plate 118 may be secured against rear wall 119 of body 10 directly using screws, clamping or other suitable means or indirectly by being sandwiched between the rear wall 119 of body 10 and the forward wall 168 of an automated actuator housing 41 (shown in FIG. 18) or the forward wall 131 of the trigger housing 109.

Coupling Shafts

In order to allow for easy, fast connection of the reciprocating shafts of each of these subassemblies to one another, a means for coupling 200 has been incorporated into the design. As illustrated in FIG. 14, valve operating rod 22 extends through the central bore 13 of sample valve body 10 and central bore 123 of back end plate 118. Just beyond the rear margin of back end plate 118, rod 22 has a thick annular groove cut around it, resulting in a section of narrow shaft. This narrow shaft is the connector shaft 170. Behind connector shaft 170 is the remaining short section of shaft, the connector cap 169.

Figure 15:
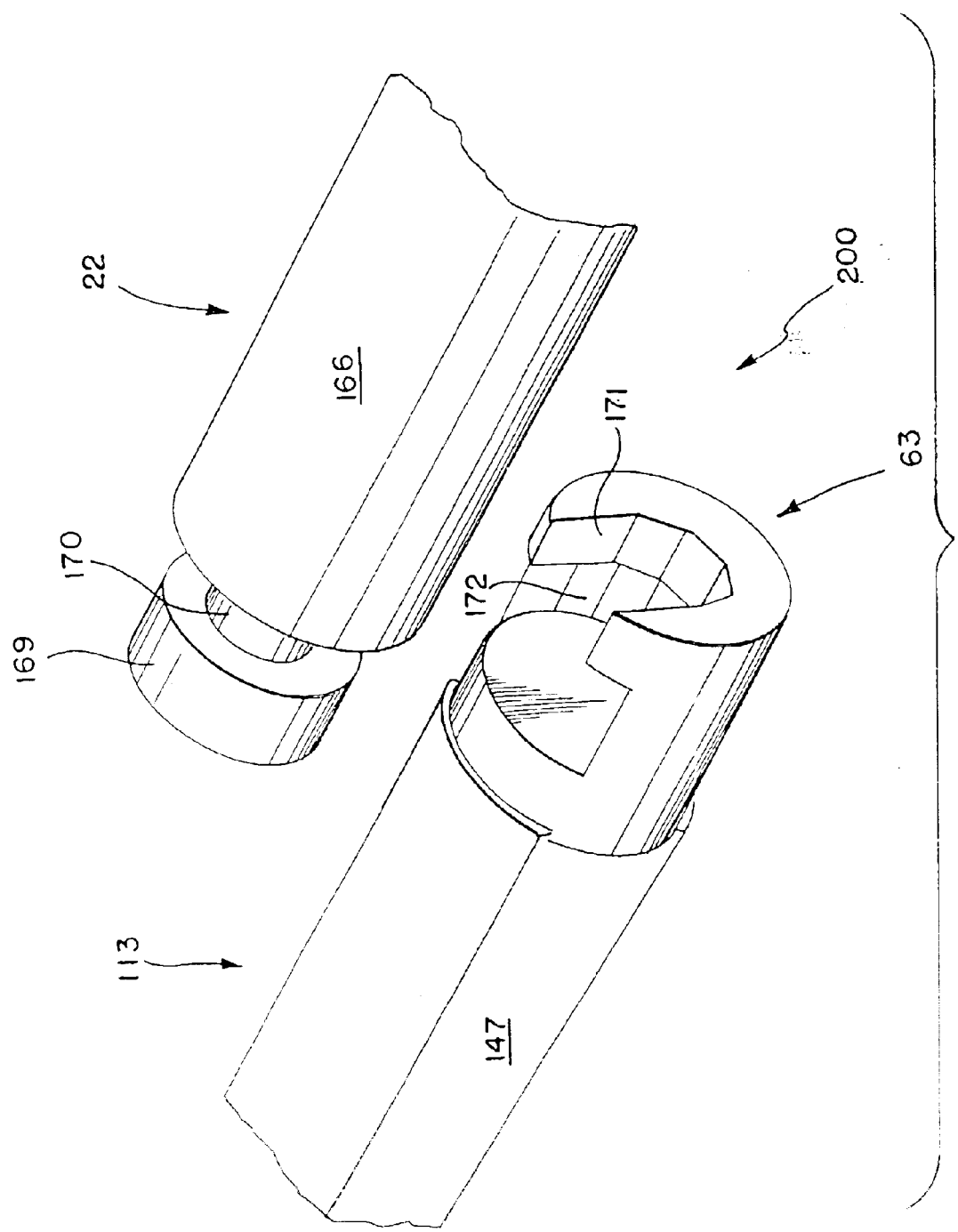
FIG. 15 is a perspective, side view of the disassembled means for coupling.
Figure 16:
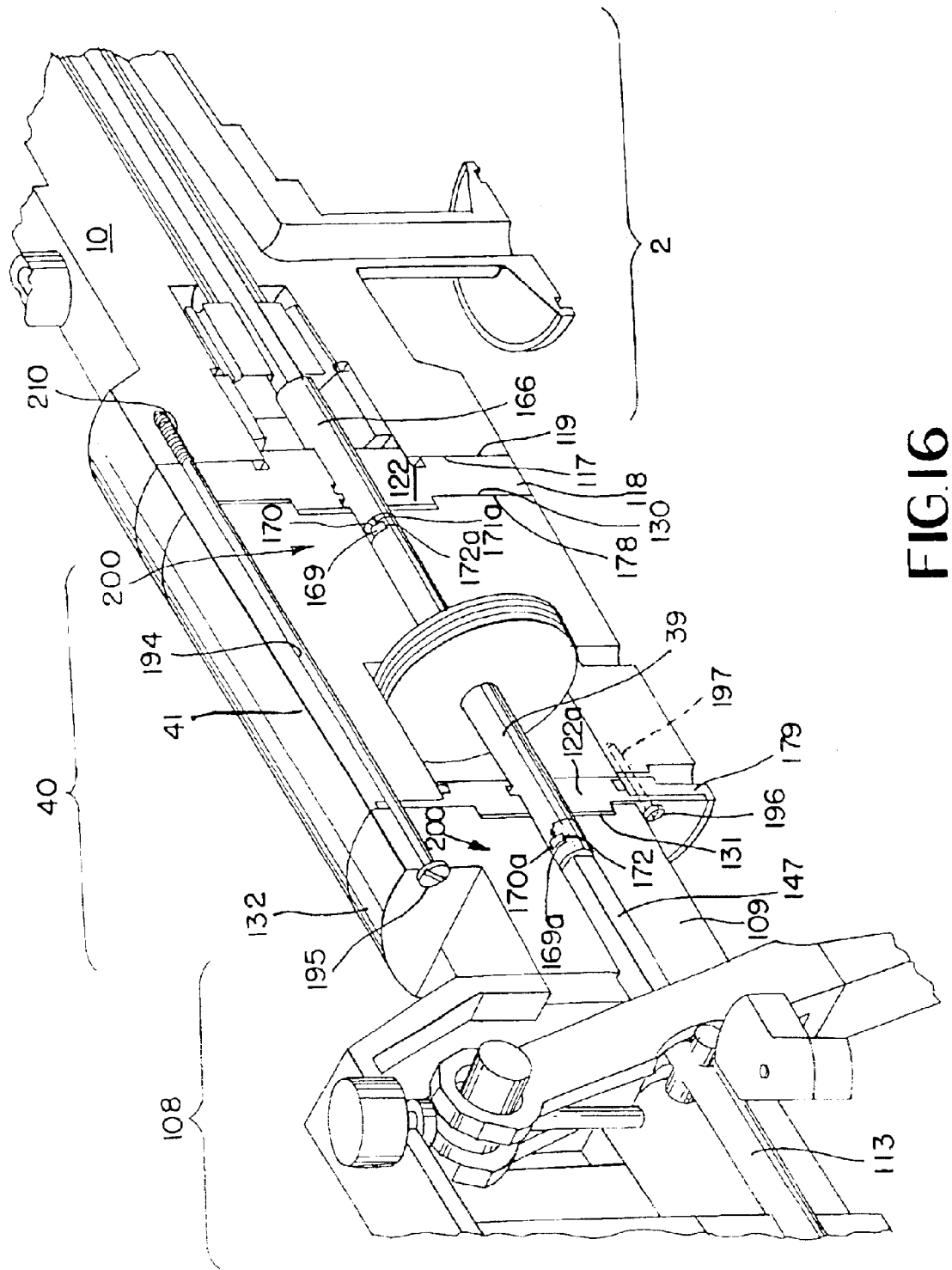
FIG. 16 is a perspective sectional view from the rear of the incorporation of an automated pneumatic actuator into the valve-manual trigger actuator assembly.

The connector cap 169 has a greater diameter then the connector shaft 170 as illustrated in FIG. 15. If the shaft with which it is to mate has a greater diameter then that of the valve operating rod 22, the diameter of connector cap need not be reduced and can have a diameter the same as that of valve operating rod 22 or larger. If, however, the mating shaft has a diameter only slightly larger, equal to or of smaller diameter then that of operating rod 22, connector cap 169 should also have a reduced diameter. However, it still must be larger in diameter then that of the connector shaft 170. This is because connector cap 169 and shaft 170 interlock in the same fashion with either the forward end of the rear valve operating rod 113 at the front part of the manual trigger actuator subassembly 108 or the forward end of the actuator piston 39 of automated actuator 40 as seen in FIG. 16. Whereas the connector cap 169 and shaft 170 form the "key", the "lock" into which they fit is formed by two perpendicular intersecting slots in the mating actuator rod.

The first slot, the shaft slot (171 on the manual actuator in FIG. 15, 171a on the automated actuator, in FIG. 16) for receiving the connector shaft, is cut into the forward end of the actuator rod in a direction parallel and down through its central longitudinal axis. The second slot, the cap slot (172 on the manual actuator, 172a on the automated actuator) for receiving the connector cap 170, is cut through perpendicular to the longitudinal axis. The result is a profile hole into which the connector cap and shaft, also having a "T" profile, can fit as illustrated in FIGS. 15 and 16.

Although these slots can be through slots, the slots of the interlocking connection shown in FIGS. 14, 15 and 16 are not. If the slots are not through slots, the resulting interlocking mechanism will be stronger, more reliable and durable. Besides the quick, easy connect-disconnect nature of this "lock and key" design, this type of connection does not have the rigorous shaft alignment requirements as do other arrangements such as threaded connections.

Once the two shafts are mated, the two subassemblies can be pushed together and secured. The interlocking connection between the two shafts will slide into the central bore of the rear subassembly where they cannot become disengaged until the subassemblies are again taken apart. This arrangement provides a safe, sure and effective connection that, once assembled, cannot inadvertently become disengaged as may be the case with some other connections.

The rear end of the automated actuator piston 39 terminates in a connector cap 169a and connector shaft 170a just like that of rod 22. This allows the user the freedom to attach the automated actuator alone, the manual trigger actuator alone or the automated actuator with the trigger actuator attached behind that, providing an automated system with manual override capabilities. Using this design, switching actuator combinations can be made quickly, easily and without modification of the equipment or interference with the valve's on-line process operation.

Actuator Attachment

As indicated above, manual and automated actuators can be used with sample valve subassembly 2 to operate the valve. The benefits of using automated operators include higher levels of reproducibility both qualitatively and quantitatively over the current manually operated equipment. There is also the benefit of attendant-free operation. But if there is a power loss, a mechanical problem or an unanticipated sampling requirement, automated systems can be clumsy or altogether non-functional. In this case, manual systems are much more dependable, less expensive and do not require the support systems, such as pressurized air, electricity, etc. Then, again, manual systems are not normally as qualitatively or quantitatively consistent and require an attendant to take a sample. Because of the variety of situations that exist and because those situations change with frequency, this system was developed to offer the operator any or all operational options without having to shut down the process to remove and modify the actuators on the valve.

The rear wall 130 of back end plate 118 and the rear wall of the automated actuator 179 are both equipped with a means for aligning and attachment to opposing housings as can be seen in FIGS. 14 and 16. The means for alignment of these subassemblies includes a short cylindrical section 122 (122a with the autoactuator) projecting rearward parallel with the longitudinal axis of the body and centered about the centerline of the actuating rods on each of the back end plate 118 and the pneumatic operator housing 41. To mate with these, the forward faces of both the pneumatic actuator housing 41 and the trigger housing 109 have similarly placed cylindrical bores or flange through holes 194 to receive them.

The means for attachment of the actuators can be as follows. The front wall 131 of the manual trigger actuator housing 109 can mate with either the back wall 130 of the back end plate 118 or the back wall 179 of the automated actuator housing 41. The front wall 178 of the automated actuator housing 41 is essentially the same as the front wall 131 of that of the manual trigger actuator housing 109, the difference being only that the lower portion of front plate wall 132 has been removed in order to allow trigger lever 111 to start further forward so that it can have a longer stroke. Both of these walls mate with the back wall 130 of the back end plate 118.

FIGS. 14 and 16 show a pattern of holes for receiving bolts with only the pattern of holes 210 within body 10 having internal threads. Furthermore, the holes in the other flanges are through holes 194 while those in body 10 are blind. In this way, body 10 can be fitted not only with the automated actuator, which, in this case, is a pneumatic operator 40, it can also be fitted with the manual trigger actuator mechanism 108 or both together. As an example, installing them both would entail positioning back end plate 118 on body 10 (if it is not already in place) followed by the pneumatic operator housing 41 on back end plate 118 which would then be followed by positioning the trigger housing 109 onto the rear wall of the pneumatic operator housing 41. Bolts 195 would then be passed from the rear through the pattern of through holes in the front plate 132 of trigger housing 109, through the same pattern of through holes in the pneumatic operator housing 41, through the same pattern in the back end plate 118 and into threaded bores 210 within body 10.

Of course, the threaded holes could be eliminated from body 10 and, instead be place in back end plate 118. Back end plate 118, itself, can be attached to body 10 in a variety of ways, including clamps, threads, etc. Here, back end plate 118 is attached to body 10 by a separate set screws 196 in back end plate 118 with a set of matching threaded holes 197 in body 10. Of course, other means by which the opposing faces of these subassemblies are secured to each other could be clamp flanges, bayonet or any other appropriate means.

Manual Trigger Mechanism

As described above, the manual actuator subassembly 108 can either be attached directly to the valve at the back end plate 118 or indirectly through the automated actuator housing 41. Similarly, the rear valve operating rod 113 which is the reciprocating member of the manual actuator subassembly, can be connected directly or indirectly to the valve operating rod 22 as described above. Unlike other manual actuators, however, this manual actuator makes use of trigger action for quicker, more precise control of sample volume and better, more reliable sample quality. The manual trigger actuation mechanism primarily comprises a retracting trigger lever which engages a transverse pin in the rear valve operating rod. As the rear valve rod is retracted, it pulls the forward valve rod attached to the sealing tip back away from the valve orifice, opening the valve.

Figure 17:
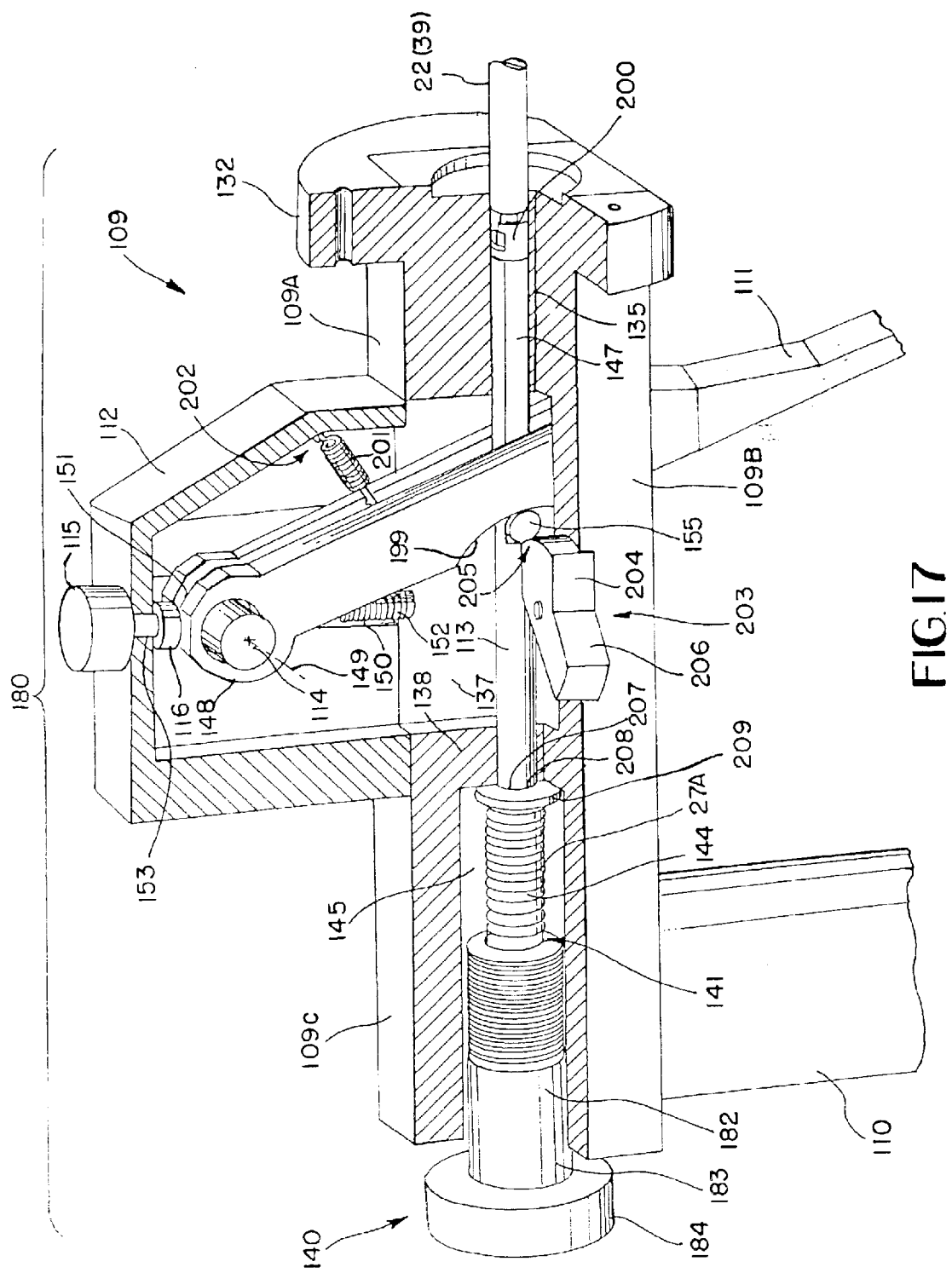
FIG. 17 is a perspective, sectional view of the manual trigger actuator assembly.

In its simplest form shown in FIG. 17, the manual trigger actuation subassembly 108 includes a trigger housing 109 having a front plate 132, two side plates, 109a and 109b and a rear plate 109c. Front plate 132 serves as the site of attachment of the trigger subassembly 108 to either the automated actuator 40 or the valve subassembly as described above. Rear plate 109c has an elongated extension which extends downwardly and which serves as a palm rest 110. Of course, front plate 132, side and rear plates 109a, b and c can all be made from one-piece.

A central longitudinal bore 135 through the housing has an axis coinciding with that of valve operating rod 22. Reciprocating within bore 135 is rear valve operating rod 113 which is attached to valve operating rod 22 either directly or indirectly through actuating piston 39 of the automatic operator by the interlocking means 200 described above. Between the two side plates 109a and 109b is the trigger lever cavity 137. Rear valve operating rod 113 extends from inside the central bore 135 in front plate 132, through cavity 137 and out the other side through the rear wall 138 of trigger lever cavity 137. Although central bore 135 extends through rear plate 109c, the rear wall of rear valve operating rod 113 can be shortened so as only to come to a point flush with the back wall of plate 109c when rod 22 and sealing tip 32 are fully retracted. Thus, when the valve is opened, because the end of the rear valve operating rod 113 is always enclosed, it cannot be interfered with or cause injury to anyone who might be near it when it is actuated.

If the return spring 27 used to keep the valve in a fail close condition is not too strong, a trigger lever 111a can be attached directly to the bottom of rear valve operating rod 113 using screws. By placing the palm of the hand on the palm rest and pulling back on the lever with a finger, sealing tip 32 can be retracted from orifice 33, thereby opening the valve. When the lever is released, return spring 27 will automatically close the valve. This design is simple, effective and relatively low cost to manufacture but it suffers from the following flaws.

First, if the return spring is strong, retracting and holding it with one or even several fingers for a period may be hard. Second, because the handle is attached directly to the shaft, if something gets in its way and nobody is around to clear it such as may be the case when using automated operation, the valve may incompletely open or close or not move at all. Also, if someone is standing in the way of the trigger lever when the automated actuator reciprocates the valve, they could be hit and injured by it. Lastly, the lever could be accidentally hit and the valve inadvertently opened. If additional cost is not as important as resolving these problems, then some or all of the following changes can be made to reduce or eliminate these weaknesses.

A more versatile alternative than direct attachment of the trigger lever to the valve operating mechanism is to provide a means by which to adjust the leverage provided by the trigger lever. This would make it easier to use without effecting the valve's sealing characteristics. This can be accomplished effectively if the trigger lever is not coupled directly onto the rear valve operating rod 113. FIGS. 2 and 17 illustrate one such arrangement.

FIGS. 2 and 17 depict a rectangular slot cut through the upper half of trigger lever 111, creating two flat parallel lever arms 146. The lever arms 146 mate with the flat lateral sides 147 of rear operating rod 113. The uppermost portion of each of the two arms of the trigger lever terminates in an annular section 148. A short transverse cam 114, as seen in both FIGS. 2 and 17, is fitted through the two annuli such that it protrudes out through the annuli 148 as shown in FIG. 17. The axis 149 of the transverse cam 114 is generally perpendicular to the longitudinal axis 144 of the rear valve operating rod 113 and cylindrical bore 135. Transverse cam 114 slides along a leverage slot 150 in housing cover 112. Transverse cam 114 contains a transverse threaded bore 151 fitted with the threaded shaft 152 of positioning knob 115. Where it extends below transverse cam 114, threaded shaft 152 extends down between the lever arms 146 of trigger lever 111.

Positioning knob 115 is fixed in housing cover 112 by the placement of the knob retainer ring 116 in an annular slot 153 on threaded shaft 152 on a side of housing cover 112 opposite positioning knob 115. The point of engagement of transverse pin 155 in rear valve operating rod 113 along the length of trigger lever 111 (and, thus, the leverage) can be set by changing the position of transverse cam 114 along leverage slot 150. The position of transverse cam 114 along leverage slot 150 is, in turn, determined by its position along the threads of shaft 152. Consequently, the operator can adjust the leverage of the trigger mechanism 108 simply by turning positioning knob 115.

As discussed earlier, rear valve operating rod 113 is attached to automated actuator 39 or valve rod 22 by the interlocking means 200. Just to the rear of slots 171a and 172a of the interlocking means 200 on rear valve operating rod 113, the sides of the cylindrical rod are milled so as to have two parallel flat opposing external walls 147. The distance between the two arms 146 of trigger lever 111 is slightly more than the thickness between the parallel walls 147 of rear valve operating rod 111. Once installed, rear valve operating rod 113 can slide freely back and forth between arms 146 of trigger lever 111 but cannot rotate because of the engagement of the flat surfaced lateral walls of rear valve operating rod 113 with the opposing flat surfaced arms 146 of trigger lever 111.

Although a non-threaded means of connection was used between rod 113 and rod 22 or piston 39, elimination of rotational motion in this design would permit threaded connections to be used. But this is not the most important aspect of this design. Because the point of engagement of the trigger lever 111 with transverse pin 155 is from the rear and because rear valve operating rod 113 can slide independently backward between trigger lever arms 146, the valve can be actuated automatically without moving the trigger lever 111. Thus, injuries can be avoided during automated operation. Furthermore, transverse pin 155 will always be correctly positioned to engage the trigger lever arms 146 when manual actuation is required. The rear margin 199 of arms 146 of trigger lever 111 where they engage transverse pin 155 have been rounded so as to reduce torque on rear valve operating rod 113 during retraction.

Trigger lever 111 is kept in the forward position and is not carried back with the momentum of an automated retraction of the rear valve operator rod 113 due to the application of forward spring tension acting on the lever arms 146. One end of a small utility return spring 201 is attached by a threaded spring anchor 202 into the inside wall of housing cover 112 while the other end is attached to the two lever arms 146 through two small holes positioned above rear valve rod 113.

To check against inadvertent actuation of the sample valve, a safety catch is incorporated into one side wall 109a of the trigger housing 109. Here, a three-position rocker switch 203 is used. When switching into the "locked" safe position, the right half 204 of the rocker switch is depressed all the way in. This makes the back portion 205 of the rocker wedge in behind the transverse pin 155, locking pin 155 from moving back. When a sample is to be taken, the operator can press on the left half 206 of rocker switch 203 to move it to the neutral unlocked position, freeing up transverse pin 155. Since rocker switch 203 is spring loaded, it will tend to stay in this position until switched again.

If the operator wishes, the valve can also be locked in the "opened" position. This can be accomplished simply by, first, pulling trigger 111 all the way back to fully retract the valve operating mechanism and fully open the valve. At this point, transverse pin 155 is behind the back portion 211 of the left half 206 of rocker switch 203. By depressing the left half of switch 203 all the way to the third locking position and releasing the trigger lever 111, the back portion 211 of the left half 206 of switch 203 will engage transverse pin 155 and hold it there as the return spring returns the valve operating mechanism forward. The rocker switch can also be color coded on the sides so that its exposed surfaces will quick indicate its status.

If adjustments to the spring tension acting on the sealing tip 32 or limitations on the stroke of the valve are desired, a secondary spring return can be incorporated by boring out the trigger housing central bore 135 behind rear wall 138 of trigger cavity 137 and threading it to make backstop bore 145. A retainer ring groove 207 is cut in rear valve operating rod 113 and retainer ring 208 added. A washer 209 is add between retainer ring 208 and secondary return spring 27a which is fitted over the back end of rear valve operating rod 113. Tension is maintained and adjusted by a threaded back stop positioner 140. Back stop positioner 140 comprises a hollow cylinder 182 with a threaded outside diameter which is attached to a cylindrical positioner knob 184 by a annular spacer 183. Parts 183 and 182 have a through bore 141 large enough to accept the diameter of the spring around rear valve operating rod 113. Knob 184 does not have a through bore but to permit independent adjustment of the back stop and spring tension, it can be bored and threaded. A threaded bolt can be adjustable threaded into it to set the back stop position. Otherwise, using backstop 140 to change the backstop position will, at the same time, change the spring tension acting on sealing tip 32 unless secondary return spring 27a is not included in the assembly. By tightening back stop 140 all the way in, it can also be used as a safety lock to prevent the seal formed between the sealing tip 32 and orifice 33 with the process from being broken unintentionally by immobilizing the valve operating rod mechanism 159 in the sealing position.

Alternative Manual Techniques

There are several other methods by which the valve rod may be actuated directly or indirectly.

1) DOUBLE PARALLEL SHAFT: An alternative to the above is to attach a second (alignment) shaft to the rear wall of the valve body 10 with a longitudinal axis parallel but not coinciding with that of valve operating rod 22. This alignment shaft extends further back so that when a finger catch or trigger lever having a rectangular upper portion with two horizontal bore holes is fitted onto the two parallel shafts and retracted to a point that, if coupled to the valve operating rod, would represent a fully open state, the end of the alignment shaft would still extend back to the rear of the rear wall of the rectangular portion.

A retainer ring or other stop is attached toward but not at the end of the valve operating rod 22. A low power secondary return spring to serve as a trigger lever return is slid onto the alignment shaft and kept in place from the rear by the attachment of a palm rest to the end of the alignment shaft. When the trigger handle is retracted, the retainer ring near the end of valve operating rod 22 will engage the rear wall of the rectangular portion of the trigger lever about the bore hole through which it protrudes and retract valve operating rod 22, opening the valve.

An advantage of this design over the one discussed earlier is that the alignment shaft minimizes torque on valve operating rod 22 and its extension. Also, the secondary spring about the alignment shaft assures that the added friction created by the addition of the trigger lever will not affect sealing performance of the valve. Further, an automatic operator can be added to the valve and operated safely, the only exposed part moving being the smooth valve rod, the reciprocating end of which can always be housed in a receiving cylinder in the palm rest. A disadvantage is that there is no means for adjusting the power required to overcome the valve return spring.

2) CABLE ACTION: Still another alternative would be to have the trigger lever rotate about a cam in a housing extending out from the rear wall of the valve body and connecting to the palm rest in the rear, the housing and the connection to the valve being similar to that described above. With one end of a cable, flexible band or other means attached to the top of the trigger lever on the opposite side of the cam from the finger catch, the cable would pass back into the palm rest, around a pulley or other similarly functioning element in the palm rest and pass forward along an axis coinciding with that of the valve operating rod 22. It would attach to the rear of valve operating rod 22 at pin. A rotational trigger lever return spring would tend to keep the trigger lever in the returned position. If the position of the cam can be repositioned along the length of the trigger lever so that the lever arm lengths can be changed, this design has all the advantages of the above as well as leverage adjustment. Various other arrangements can be arranged using gears assemblies, including rack and pinion designs. These can, however, become complex and expensive, with several moving parts.

Pneumatic Control

The pneumatic automated actuator 40, illustrated in FIGS. 3 and 16 is controlled by the control means 4. This control means 4 can cause movement of the valve operating rod 22 by actuating the pneumatic actuator 40 (in this case, through electromagnetic actuator 212 and pressurized air 213) in order to reciprocate the valve operating rod 22 in the central bore 13. When the manual trigger mechanism is attached to the rear of the pneumatic actuator as was discussed above, and if, for some reason, the control means or automatic actuator should fail, an operator could simply reciprocate the valve using the trigger lever. If the actuator 40 is connected but not to the trigger lever mechanism, the operator could grasp the "keyed" rear end of pneumatic operator piston 39 protruding from the rear of the actuator and use that to actuate the system. Lastly, if the valve is installed with neither the automated actuator or manual actuator available, the valve can still be operated by levering or otherwise grasping and pulling back on the "keyed" end of rod 22 protruding from the rear of the valve.

Probe and Sensor

Returning to FIGS. 2 and 3, a probe 20 is indicated within a probe orifice 19 of the drain passage 14. This probe 20 and orifice 19 can alternatively be located in the sample cavity 11 or alternatively within both the drain passage 14 and sample cavity 11. The probe 20 can be a temperature and/or pressure probe. This probe 20 is operatively connected to the means for detecting 4a of the control means 4.

The means for detecting 4a and probe 20 can provide for independent verification of the various aspects of the system's operation. By comparing a profile of a sampling system temperature or pressure when the system is operating correctly with profiles when various components of the system fail, a determination can be made by the means for detecting 4a of a system failure (abnormal operation). Moreover, a determination can be made by the system as to the severity of the failure and whether to abort further sampling cycles as well as to sound an alarm. The temperature or pressure profile is captured from the probe 20 and fed to the means for detecting 4a. Accordingly, if the diaphragm 49, for example, were to rupture, the probe 20 could determine this condition. Moreover, if there was blockage in the inlet passage 12, this condition could be detected. The means for detecting 4a with the control means 4 can initiate appropriate action. This probe 20 can also detect if an adequate steam temperature has been reached during the sterilization cycle.

Sample Collection

Returning to FIG. 3, downstream from the drain passage 14 is means for collecting sample 51 and a means for collecting drain 52. The means for collecting a sample 51 includes sample drain valve block 8. This valve block 8 has a diaphragm pneumatic valve 93 connected to the sample collector 94. This sample collector can be a sample vial subassembly, for example. Also connected to the diaphragm pneumatic valve 93 is an electromagnetic valve 95 with a pressurized air source 96.

The drain valve block 9 includes a diaphragm pneumatic valve 97 connected to a disposal means 98. Also connected to the diaphragm pneumatic valve 97 is an electromagnetic valve 99 and a source 100 of pressurized air. Similarly to the valves 67, 71 and 75, the diaphragm pneumatic valves 93 and 97 can be replaced by any known valves. Likewise, the valves 95 and 99 could also be replaced by other valves or the valves 93 and 95 and the valves 97 and 99 could be combined into a single unit. The electromagnetic valves 95 and 99 are operatively connected to the control means 4 as indicated in FIG. 3.

Feed/Drain Lines

Figure 18:
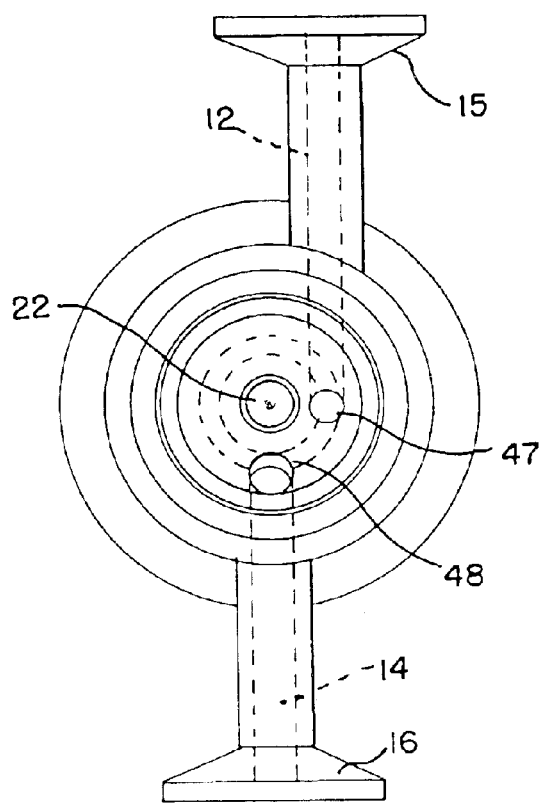
FIG. 18 is a schematic end view showing the inlet passage and outlet passage.
Figure 19:
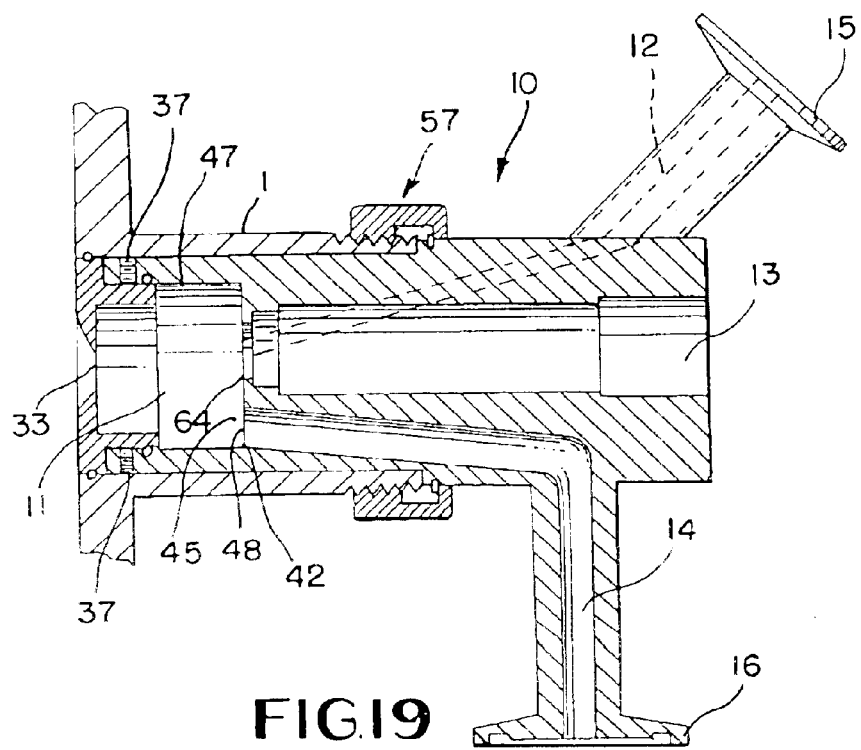
FIG. 19 is a side, sectional view illustrating the positioning of the inlet passage and drain passage of the apparatus of the present invention.

Turning now to FIGS. 18 and 19, configuration for the inlet passage 12 and drain passage 14 will be described. To one side of the central bore 13 for the valve operating rod 22 is the inlet passage 12. This inlet passage declines towards the sample cavity 11.

Furthermore, the surfaces facing into the sample cavity 11, when endcap 44 is in place, generally are angled in a declining fashion such that flow is down and out of sampling cavity 11 through declining drain passage 14. Thus, gravity alone will insure complete drainage of any material entering the valve through either inlet passage 12 or orifice 33 down and out through drain passage 14. Inset within the base of the sample cavity, leading away from the lower rear point of sealing of o-ring 17 in groove 36 of cap 44 with body 10, is a drain collection trough 42 declining to and through opening 48 from internal cavity 11 into drain passage 14. Drain collection trough 42 can actually be an opened extension of drain bore 43 up and into a side of the sample cavity 11, rather than terminating flush with the rear wall at opening 48 into sample cavity 11 as can be seen in FIG. 19. In fact, the collection trough 42 can extend up to the front of the sample cavity 11 if so desired. Thus, drain collection trough 42 and drain passage 14 incline downwardly away from the sample cavity 11. Likewise, inlet passage 12 can also be extended forwardly through the side wall to thereby terminate at or near the forward wall of the sample cavity. In FIG. 2a, the entire internal cavity of body 10 forms a drainage basin which drains down from all sides to the opening to drain passage 14. With a path between lowest point of the opening of orifice 33 always having an unobstructed profile that descends at an angle greater than that of the ferrule in which it is installed and with the back wall behind the drain 14 also sloping to that opening, the latest embodiment provides an effective means for removing fluid (without pooling or hold up within the valve body) from vessel and conduits, even when retrofitted into upwardly slanted ferrules.

In FIG. 18, the cap 44 has been omitted and the offset of the feed inlet 47 to the sample cavity 11 can be seen. It should be appreciated that central bore 13 may also be offset when physical size constraints in valve design require it (also illustrated in FIG. 19). At such times, orifice 33 of cap 44 will be similarly offset so as to align with the blunt sealing tip 32 of diaphragm 49 positioned on valve operating rod 22. It has been shown that the cap 44 can be made an integral part of body 10, that a means to feed (including feed inlet 47) may not be a necessary inclusion in the device and that neither the feed inlet 47 (if present) or the means for draining (including drain bore 43) may not need to be offset from a (vertical) plane through the central axis of the valve body.

As can be seen in FIG. 19, the angle of inclination for the drain passage 14 is less than the angle of inclination for the inlet passage 12. Of course this relationship of the angles between the drain passage 14 and inlet passage 12 can vary. For example, a greater angle between the drain passage 14 and axis of the body can be provided than between the inlet passage 12 and the axis of body 10.

Due to the positioning of the inlet passage 12 above the drain passage 14, the position of declining drain collection trough 42 leading through opening 48 to become drain passage 14 as well as the smooth, flush transition between the drain passage and the bottom wall of drain collection trough 42 all with respect to sample cavity 11, a means 45 for preventing accumulation of material in cavity 11 is formed. This means will enable free flow of the sample from the sample cavity 11 to the drain passage 14. Pooling of the sample will be avoided. Therefore, possible contamination of subsequent samples is avoided.

Also, drain passage 14 has an internal diameter of generally 6 mm. This is generally larger than the biggest sample particle drawn from vessel 53. In that way, clogging of the drain passage 14 is avoided. While maximum sample particle size is one variable to be considered when designing a valve for retrofit onto a vessel, other variables defining the configuration of the existing ferrule that will receive the valve are also important. Below a mathematical relationship which includes these variables will be discussed, showing how the variables may affect each other and how this can be used to define critical parameters for a free-draining valve.

As seen in FIGS. 18 and 19, due to the offset mounting of inlet passage 12 and outlet passage 14, it is possible, for example, to squeeze each of these items within the 25 mm constraint for the outer diameter of body 10. In this manner, the body 10 can be retrofit into an existing apparatus. As noted above, the inner diameter of ferrule 1 is typically 25 mm in many devices. While this dimension can change, it should be understood that the instant invention can be inserted into existing equipment without the need for retrofitting this equipment. Of course, when larger or smaller ferrule ports exist, the instant invention can be made larger or smaller to accommodate these ferrules with correspondingly larger or smaller components.

As seen in FIG. 2a, the inlet passage 12, drain opening 14 and drain trough 42 all can be accommodated within the arrangement shown without planar offset. In other words, all feed and drain can be coaxial and/or coplanar, but such an arrangement is not mandetory. This arrangement would provide a greater flexiblility with the axis of the body.

Angles of Installation

In FIGS. 20–22, mounting of the apparatus of the instant invention is schematically represented. If the instant apparatus is to be mounted in a horizontally oriented ferrule 1 as shown in FIG. 20, the longitudinal axis 65 of the body 10 will be generally horizontal. The longitudinal axis 59 for the inlet passage 12 will be offset from axis 65 by an angle of approximately 18.5°. The longitudinal axis 58 for the drain passage 14 will be offset from the longitudinal axis 65 of the body by approximately 3°. Therefore, the slope for the inlet passage 12 is greater than the slope for the drain passage 14. This helps to ensure proper drainage of the sample, steam, air, wash medium and/or condensate.

As shown in FIG. 21, if the ferrule 1 is sloped downwardly, for example, by 15° from the horizontal plane h, the longitudinal axis 65 of the body 10 will similarly be offset by 15°. Such a downward slope of 15° is a standard design for some ports in vessels or conduits 53. With this downward inclination, the longitudinal axis 58 of the drain 14 will be offset about 18° from the horizontal plane h. The longitudinal axis 59 of the inlet passage 12 will continue to have a downward slope. This axis 59 will be offset from the horizontal plane h by approximately 3.5°. Therefore, with a downwardly oriented ferrule 1, proper flow can continue to be had with the instant invention. Pooling of the sample and steam, air, wash medium and/or condensate can be avoided in this arrangement.

In the upwardly inclined ferrule 1 of FIG. 22, the longitudinal axis 58 of the drain would have less of a slope than the longitudinal axis 59 of the inlet passage 12. Nonetheless, this arrangement continues to urge material through the system. For situations where the ferrule is sloping upward at an angle greater then the 2°, effective drainage can be accomplished in either of two ways. The first is by means of extending a tube up to orifice 33 and overpressuring the valve, in effect, vacuuming the sample out by the low pressure created around the mouth of the extension of the drain line. The second method is to have a greater angle of declination on the drain line and a lesser angle of inclination to the feed line.

Determining whether or not a valve can be retrofitted to an existing port can be done using the relationships described earlier. The latest embodiment described above provides a means by which material may be removed through an upward sloping ferrule, contrary to intuition. For example, a ferrule with a upward slope of 15 degrees, a length of 1.0" and a diameter of 1.0" can be fitted with a valve with an orifice having at least 0.25" diameter with a sealing face about the orifice of over 0.4" in diameter and with a internal drainage trough which has a declining slope of at least 16 degrees. When installed in the ferrule, this valve has a net declination to its internal profile. This, in conjunction with the smooth, declining orientation of the internal cavity sides and rear wall leading back to seal face 320 combine to make this an effective fully drainable valve even in this orientation.

In the present application, longitudinal axis 59 of inlet passage 12 may decline by as much as 90 degrees, but at least by an amount greater than the amount of inclination of the ferrule. Similarly, the longitudinal axis 58 for drain passage 14 may decline by as much as 90 degrees, but at least by an amount greater than the amount of inclination of the ferrule. While flow related problems are less of a concern with horizontal and declining ferrule installations, it is potentially a much more serious problem with inclined ferrules. The trend in the industry is toward inclined ferrules, particularly those at 15 degree angles of inclination. With the incorporation of end cap 44 into body 10, eliminating the junction between these two and the creation of a drain trough 42 formed with the bottom of sample cavity 11 with all surfaces draining down to and exiting through drain opening 14, the potential for sample and process contamination due to sample hold up and carry over in crevices and pooling on non-draining surfaces has been minimized. Unlike other designs, this is not dependent on flushing material out through multiple washes or high pressure flows. This most recent embodiment has its surfaces optimized to promote free and full drainage.

Process Control

Process control for the instant invention is carried out under the direction of the control means 4. As noted above, this control means 4 can be a programmable logic controller, computer operated controller or any other suitable control means. The control means 4 permits the appropriate sequencing of the various valves of the instant invention. Collectively, the system sequences and times the opening/closing of each valve as well as the sampling device but will allow an operator to program the length of time each valve will remain open. This provides a means by which the process control system can be adapted and incorporated into a variety of different process applications.

Different sized valves, different materials of construction, different process flow temperatures and flow rates different cleaning or chemical agents (steam, air, wash medium, etc.) and other process materials can influence the proper timing of the various facets of operation (sampling, cleaning, sterilizing, resampling, etc.). A single cycle sequence of the basic components of the system of the instant invention will now be discussed.

The control means 4 controls the functioning of the main sample subassembly 2 in tandem with the five peripheral process flow control valves 5, 6, 7, 8 and 9. The control sequencing is laid out in FIGS. 25 and 26. This sequence is designed to clean and sterilize the inlet passage 12, main sample subassembly 2 and drain passage 14 before each sampling. This system will also purge the last of the sampling material into the disposal means 98. After the blunt sealing tip 32 closes orifice 33, the system will also be cleaned and resterilized between each sampling.

The pure steam feed block 5, for example, will control the flow of steam to sterilize the system. Likewise, the pure air feed block 6 will control the flow of pure air through the system for two purposes. First, this air will be blown through the inlet passage 12, sample cavity 11, drain passage 14 and to the disposal means 98 such that any sampling material that might remain after a sampling is removed. This air is also blown down the drain passage 14 such that any steam condensate that remains after the sterilization phase is completely removed. The pure air will both cool and dry the sampling system before the next sample is taken. The wash medium can be provided by the wash medium valve block 7 to clean the system if steam is insufficient. Likewise, a combination of steam and wash medium can be used. The pure dry air 70 can also be used to help flush the wash medium from the system and to dry the system after the use of wash medium.

The drain line block 9 will be open to drain away condensate, wash medium and the like during cleaning and sterilization. The sample vial block 8, on the other hand, will be open to allow the sample material to flow into the sample collector 94.

Figures 25, 26:
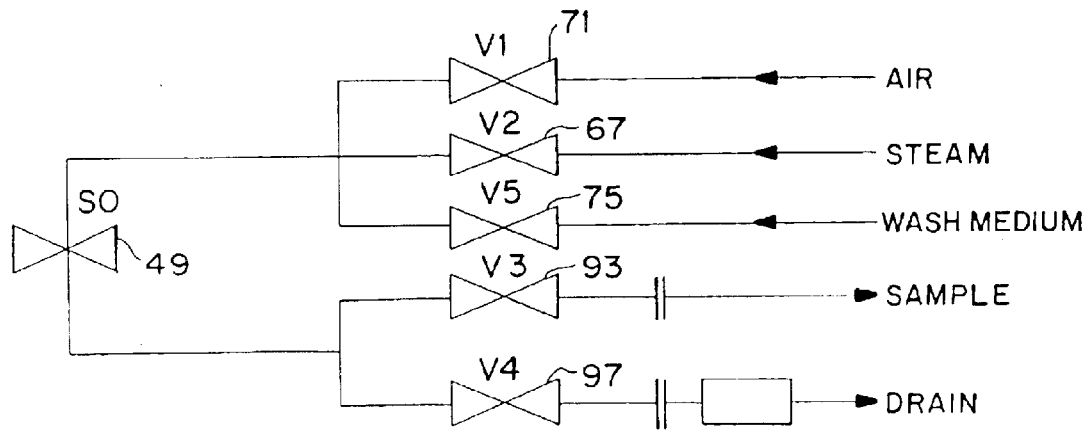
FIG. 25 is a schematic view showing the operation of certain valves in the instant apparatus.
FIG. 26 is an example of a timing chart for one operation of the instant invention.

In FIG. 25, valves 49, 71, 67, 93 and 97 are indicated by S0, V1, V2, V3 and V4, respectively. As indicated in FIG. 26, a waiting period will first be encountered during one type of sampling operation. The valve indicated as V1 and V4 will be open. In other words, the diaphragm pneumatic valves 67 and 97 will be open. Steam will rush from source 66 through inlet passage 12, sample cavity 11 and out drain passage 14 to the disposal means 98 while valve 97 is still open. After an appropriate period of time, the valve 67 will be closed and the valve 71 will be open. Pure dry air can then rush through the system to the disposal means 98. This pure dry air will not only force any remaining particulate matter through the system but will also aid to cool and dry the interior of the apparatus.

In the timing chart of FIG. 26, a one-second delay is then indicated. It should be recognized that this delay could be omitted or could be for a shorter or longer duration. Sampling will next take place. In this arrangement, the valve S0 and V3 are indicated as being open. In other words, the valve 49 will be opened to permit the sample to exit the vessel or conduit 53 through the port 54 thereof. The material will move through orifice 33 into sample cavity 11 and down drain 14 to the sample collector 94. While it is not shown in the FIGS. 25 and 26 arrangement, it should be noted that the valve 93 can initially be closed and the valve 97 opened such that a first portion of the sample will actually go to the disposal means, if so desired. In any case, valve 97 should close before valve 93 opens.

No valves are provided in the interior of the sample cavity 11 for preventing the sample from entering the inlet passage 12. The valves 67, 71 and 75 will be closed such that an internal pressure will be sufficient to prevent the sample from traveling up inlet passage 12. Moreover, gravity also prevents the sample from traveling up the inlet passage 12. The apparatus A is therefore simplified and can be used in existing vessels or conduits 53 without modification due, in part, to the omission of extra valves. In other words, the relatively small size of body 10 can be maintained such that it is compatible with existing vessel or conduit ports. Moreover, potential sites of contamination are avoided by omitting such additional valves.

After a sufficient sample has been collected at collector 94, another one-second delay is indicated in FIG. 26. Again, no delay or a greater or lesser time period can be provided. The valve 49 indicated by S0 in FIG. 26 is then closed and the valve 71 is opened. Pure dry air will then rush through the system in order force the sample in cavity 11 and drain passage 14 into the sample collector 94. Accordingly, one operation of the apparatus of the instant invention has been described. It should be understood that the wash medium valve block 7 can also be operated if so desired. However, in the arrangement of FIG. 26, the wash medium from source 74 is not used.

As previously noted, the arrangement in FIG. 24 (and FIG. 3) shows the body 10 of the apparatus being inserted into a vessel or conduit 53. When stagnant layers 60 may be present in the vessel, a mounting arrangement shown in FIG. 24 can be used. This design places orifice 33 beyond these stagnant layers 60. The apparatus used in the design of FIG. 24 is similar to the arrangements of FIGS. 2, 13A or 13B. If the user will never install the valve in a penetrating fashion, the cap 44 need not have two o-rings and grooves on its outside circumference and cap 44 need not be quite as long as is shown in these figures. However, if two grooves are used, a single o-ring 34 can be moved between the two grooves 35 or 35a as needed. Of course, two separate o-rings could be provided, one for each groove. However, when the apparatus A is positioned as shown in FIG. 24 (or FIG. 3), it is preferred to omit an o-ring from the forward groove 35. In this manner, it is less likely that material would become trapped at the forward, outer end of the cap 44.

It should be appreciated that after the body 10 is mounted in the arrangement of FIG. 24, this body 10 is not movable once mounted. Rather, it extends within the vessel or conduit 53 for the predetermined distance indicated during its operation. Of course, when this device is no longer needed, the means 57 for coupling can simply be detached and this apparatus removed from the vessel or conduit 53 and readjusted. Due to the forward o-ring groove 35, this body 10 can be mounted substantially flush with the wall 61 of the vessel or conduit 53, too. The o-ring groove 35a with o-ring 34 will form a seal between body 10 and vessel or conduit 53 when the apparatus A is extended as shown in FIG. 24. Alternatively, when the face of cap 44 is generally flush with the interior 61 of vessel or conduit 53, an o-ring in groove 35 will form a seal between the apparatus A and the vessel or conduit 53. The o-ring 34 can be moved from the rearward groove 35a to the forward groove or a new o-ring 34a can be inserted in groove 35 while the rearward groove 35a may or may not retain the o-ring 34.

Feed/Inoculation Means

Up to this point, the instant invention has been discussed as a sampling apparatus. As shown in FIG. 23, this instant invention can also be used as a feed/inoculation means. In FIG. 23, the apparatus A is mounted on the top of vessel 53. When used as a feed/inoculation apparatus, the instant invention can also be mounted on the side of vessel 53.

The feed/inoculation arrangement shown in FIG. 23 is similar to the sampling arrangement previously discussed. However, the drain passage 14 extends well into the sample cavity 11 to prevent pooling of the sample or cleaning material in this arrangement. The opening 48 for drain passage 14 is generally adjacent the wall of cap 44 having orifice 33.

As indicated in FIG. 23, means 101 is provided for feeding the sample. This means 101 will supply the sample through the inlet passage 12, sample cavity 11, orifice 33 and into the vessel or conduit 53. After the sample has been charged to the orifice or conduit 53, the sealing tip 32 can be moved to close orifice 33. Then the supply means 50 can feed steam, dry air and/or wash medium through the inlet passage 12, sample cavity 11 and out of the drain passage 14 to the means for collecting drain 52.

Indicated schematically in FIG. 23 is a switching means 102 utilized with the supply means 50 and means 101 for feeding sample. This means 102 selects whether the means 101 will supply the sample through the inlet passage 12 or whether the supply means 50 will clean and/or sterilize the inlet passage 12 and other downstream structure.

Apart from having the end 48 of the drain passage 14 located at the end of the sample cavity 11, the diameter of the drain passage 14 is of a sufficiently small diameter such that the pressure in sample cavity 11 (created from inflow through passage 12) will be sufficient to force any material fed through inlet passage 12 up and out drain passage 14. In this manner, the particle size of the sample fed to the sample cavity 11 is limited by the size of the inlet passage 12. When the supply means 50 is operated, sufficient air, steam, and/or wash medium can be fed through the inlet passage 12 in order to force any sample or other contaminant through the drain passage 14 to the means for collecting 52. Otherwise, the design of the feed/inoculation arrangement shown in FIG. 23 is similar to the sample assembly previously discussed.

Advantages

The instant apparatus A has several advantages. Its geometry will enable the body 10 and its contents to be relatively small such that it can be retrofitted into existing vessels or conduits. For example, the 25 mm standard size for ferrules 1 can be accommodated with the instant invention.

The instant invention provides a uniquely designed biocompatible, resterilizable flexible diaphragm which allows the sample extraction orifice to be flush mounted with or penetrated into the vessel or conduit 53. A customized subassembly design is possible in which all of the contamination-prone opposing sliding/rotating surfaces are sealed from the sample. For example, the bellows 30 separates and isolates a sample from the operating portions of the valve 49. Other control features such as the steam feed valve block 5, pure dry air valve block 6 and wash medium valve block 7 are removed from the sample. Since contamination-prone parts are removed from the process, the instant apparatus A is a more effective overall sanitary design.

The instant apparatus A is free-draining and will avoid pooling. Pockets between the sample cavity 11 and the drain passage 14 are not present such that pooling or accumulation of a sample or drain is further avoided.

With the exception of seals about the cylindrical sealing portion 166 of rod 22, all secondary seals are static to provide the most effective barrier to leakage within the system and/or to the outside environment. Further, the interfaces between the abutting surfaces on the process side (where crevice-related carryover contamination often occurs) are sealed with the static seals (with the exception of the specially designed primary seal which is a diaphragm-type seal). The instant invention avoids the need for dynamic o-ring seals. Void volume in the sample cavity 11 is minimized. Tortuous flow is also avoided. Therefore, minimal loss of sample material during the sampling process and maximized reproducibility and accuracy of measured samples is had with the instant invention. By using small volumes, only small errors in measurements will be made.

Within this 25 mm outside diameter design discussed, the instant design permits particles of at least six mm outside diameter particles to pass from the vessel or conduit 53 through the sample cavity 11 and out of the drain line 14 to the sample collector 94. Therefore, physical distortion of the sample constituents is avoided, thereby assuring that samples taken are not biased due to size exclusion.

The trigger mechanism, which allows the valve to be rapidly opened and closed, allows more precise control of sample volumes and, at the same time, reduces sample waste. Furthermore, because sample volumes can be controlled much more precisely, even small volumes, operators will not have to resort to "throttling" which can cause physically and chemical changes in samples through shear. Lastly, the trigger actuator mimics the action of automated actuators. This means that its samples will correlate better with those taken using automated actuators then will other manual actuator designs.

The trigger mechanism and or the automated actuator can readily be added or removed from the valve, providing easier maintainability. Furthermore, because the valve is sealed and has the primary return spring within, these change-out operations can be done without affecting the valve's on-line service.

All static threaded connections and abutting surfaces of the instant invention are placed behind static o-ring seals. This removes trouble-prone interfaces from contacts with process flow.

The control means 4 and means for detecting 4a of the instant invention provide for automatic sampling or inoculation. Therefore, operator error is avoided. Manual override also permits sampling even in the case of power failure.

Pressure or temperature profiling of the system and independent indirect verification enables a more reliable operation.

Accordingly, with the instant invention, an accurate subsample of the process composition can be had. This arrangement can be used with existing systems or with new systems. Maintenance of the instant apparatus can easily be carried out.

Because the body 10 of the instant invention can be machined from a single piece of metal, plastic or other material, if so desired, the need for additional junctures is eliminated. This also avoids potential points for contamination to the sample. Also, the bulb design of the sealing tip 32 avoids dead space.

Due to the control means 4, the timing sequence can easily be changed. For example, an operator can change the length of each of the phases in the sampling process and, using feedback from the temperature and/or sensor probe 19, determine if any error has occurred in the system.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A valve for insertion into a ferrule having a given internal diameter, the valve having a sample cavity, a sampling orifice and a drain outlet, the sampling orifice and drain outlet being operatively connected to the sample cavity, a diameter of the sampling orifice being determined by the following formula:

Dov< or =Dfv−[(Dr1+Dr2)+(Dv1+Dv2)+(Dw1+Dw2)+(Ds1+Ds2)+Div+Ddv], wherein Dov is the diametric height for orifice construction, Dfv is the ferrule bore diametric height, Dr1 and Dr2 are the diametric spaces required to seal a body of the valve with a bore of the ferrule, Dv1 and Dv2 are the diametric spaces required to form upper and lower margins, respectively, of an annular wall of the valve body, Dw1 and Dw2 are the diametric spaces required to form an outer wall at the upper and lower margins of the valve body, respectively, Ds1 and Ds2 are the diametric spaces required to allow for an intersticial space between an inside diameter of the ferrule and an outside diameter of the valve body along the upper and lower margins of the valve body, respectively, Div is the diametric height lost due to an inclination of the bore, and Ddv is the diametric height to assure channel drainage.

2. A valve for insertion into a ferrule having a given internal diameter, the valve having a sample cavity, a sampling orifice and a drain outlet, the sampling orifice and drain outlet being operatively connected to the sample cavity, a diameter of the sampling orifice being determined by the following formula:

Dov< or =Dfv−[Div+Ddv+C], wherein Dov is the diametric height for orifice construction, Dfv is the ferrule bore diametric height, Div is the diametric height lost due to an inclination of the bore, Ddv is the diametric height to assure channel drainage, and C is a constant for a particular application including the diametric height for wall thickness, the diametric height for sealing arrangements, the diametric height for interstitial spaces and the diametric height for an annular seal.

3. A valve installed in an inclined ferrule, comprising:
a valve body;
a drainage trough formed in said valve body; and
an orifice, said orifice opening at a front of the valve body, a lower margin of said orifice forming a beginning of said drainage trough, said lower margin being located at a predetermined point along a length of an internal bore of the ferrule,
wherein a vertical plane passing through said predetermined point on the lower margin passes through a point along a bottom margin of the bore of the ferrule, and Lf is a length from a point at a rear margin of the ferrule to said point along said bottom margin, and
wherein in order for a freely draining trough to be formed in the valve body from the lower margin of the orifice to the rear margin of the ferrule, a vertical position of the lower margin must be higher than a value of Div calculated at said point along the bottom margin, for a flush-mounting valve, the value of Div being determined by:

$$Div = Lf\ SIN(Aa)$$

where Aa is an angle of an axis of the bore of the ferrule.

4. A valve installed in an inclined ferrule in a wall of a vessel or conduit, an axis of an internal bore of said ferrule having an angle of inclination in a direction away from the vessel or conduit, comprising:
a valve body, said valve body having an internal drainage path with an angle of declination in a direction away from the vessel or conduit greater than or equal to said angle of inclination of said axis of said internal bore of the ferrule, a forward end of said internal drainage path having an orifice; and
a valve operating rod having a sealing tip engageable with said orifice for opening and closing said orifice, said valve operating rod having an axis at an angle to an axis of said internal drainage path.

5. The valve according to claim 4, wherein said angle of declination of said drainage path of said valve body includes an additional angle of declination Ab, wherein a total angle of declination of the drainage trough is the sum {(−Aa)+Ab}, wherein Aa is the angle of inclination of the internal bore of the ferrule.

6. The valve according to claim 4, wherein, said orifice opens into a process, said drainage path beginning at a lower margin of said orifice and passing above and beyond a lower rear margin of the ferrule.

7. The valve according to claim 4, wherein said orifice opens into a process within the vessel or conduit, and wherein said drainage path begins at or adjacent to a lower margin of said orifice and passes above and beyond a lower rear margin of said ferrule.

8. The valve according to claim 4, wherein said valve body includes an orifice formed in a forward portion thereof, said orifice opening into a process within the vessel or conduit, and wherein said drainage path begins at or adjacent to a lower margin of said orifice and continuously declines at least until an exit of said valve body.

9. The valve according to claim 4, wherein said valve body includes an internal cavity therein with a sampling orifice located at a forward portion thereof, said valve body and said orifice each having a longitudinal axis extending through a center thereof, respectively, said longitudinal axis of said valve body being offset from said longitudinal axis of said orifice.

10. The valve according to claim 4, wherein a longitudinal axis of said orifice is offset from the axis of the internal bore of the ferrule.

11. The valve according to claim 10, wherein said longitudinal axis of said orifice is offset above the axis of the internal bore of the ferrule.

12. The valve according to claim 10, wherein the longitudinal axis of said orifice is generally parallel to the axis of the internal bore of the ferrule.

13. A valve assembly, comprising:
a ferrule installed in a wall in a vessel or conduit, said ferrule having an internal bore having an angle of inclination in a direction away from the vessel or conduit, said internal bore having a first, process side and a second, non-process side;

a valve fitted into said internal bore of said ferrule, said valve having a valve body with an internal cavity, said valve body having an orifice in a front wall thereof, said orifice opening to said process side of said internal bore of said ferrule, and a drain passage opening to the rear thereof, said drain passage being connected to the orifice by a drainage trough, said drainage trough beginning at a bottom margin of the orifice and ending at an opening of said drain passage, said drainage trough continuously descending in a direction away from the vessel or conduit at an angle greater than or equal to the angle of inclination of the internal bore of said ferrule and passing above a lower rear margin of the internal bore of the ferrule, said valve further comprising a valve operating rod having a sealing tip engageable with said orifice for opening and closing said orifice, said valve operating rod having an axis at an angle to said drainage trough.

14. The valve assembly according to claim 13, wherein a longitudinal axis of the internal bore of the ferrule is offset from a longitudinal axis of the orifice.

15. The valve assembly according to claim 14, wherein said longitudinal axis of said orifice is offset above the longitudinal axis of the internal bore of the ferrule.

16. The valve assembly according to claim 13, wherein said valve body and said orifice each have a longitudinal axis extending through a center thereof, respectively, said longitudinal axis of said valve body being offset from said longitudinal axis of said orifice.

17. An apparatus for moving a sample of a flowable material through a ferrule in a wall of a vessel or conduit, comprising:
 a ferrule mounted in a wall of a vessel or conduit, said ferrule having an internal bore, said internal bore being inclined such that a center of an opening of said internal bore into the vessel or conduit is lower than a center of an opening of said internal bore to an outside of said vessel or conduit;
 a valve installed in said internal bore of said ferrule, said valve including a valve body, said valve body having an internal drainage path, said internal drainage path having an angle of declination greater than or equal to the angle of inclination of the axis of the internal bore of the ferrule, said valve further comprising an orifice at a forward end of said internal drainage path and a valve operating rod having a sealing tip engageable with said orifice for opening and closing said orifice, said valve operating rod having an axis at an angle to an axis of said internal drainage path.

18. The apparatus according to claim 17, wherein said orifice opens into a process within the vessel or conduit, and wherein said drainage path begins at or adjacent to a lower margin of said orifice and passes above and beyond a lower rear margin of said ferrule.

19. The apparatus according to claim 17, wherein said orifice opens into a process within the vessel or conduit, and wherein said drainage path begins at or adjacent to a lower margin of said orifice and continuously declines at least until an exit of said valve body.

20. The apparatus according to claim 17, wherein a longitudinal axis of said orifice is offset from the axis of the internal bore of the ferrule.

21. The apparatus according to claim 20, wherein the said longitudinal axis of said orifice is offset above the longitudinal axis of the internal bore of the ferrule.

22. The valve according to claim 20, wherein the longitudinal axis of said orifice is generally parallel to the axis of the internal bore of the ferrule.

23. The apparatus according to claim 17, wherein said valve body and said orifice each have a longitudinal axis extending through a center thereof, respectively, said longitudinal axis of said valve body being offset from said longitudinal axis of said orifice.

24. A valve for use in a vessel or conduit, the valve comprising:
 a valve body having an internal cavity with a sampling orifice located in a forward portion thereof, a bottom of said internal cavity continuously declining from at or adjacent to a lower margin of said orifice to at least an exit of said valve body, said valve body and said orifice each having a longitudinal axis extending through a center thereof, respectively, said longitudinal axis of said valve body being generally parallel to and offset from said longitudinal axis of said orifice.

25. An apparatus for moving a sample of a flowable material through a ferrule in a wall of a vessel or conduit comprising:
 a ferrule mounted in a wall of a vessel or conduit, said ferrule having an internal bore, said internal bore having a longitudinal axis;
 a valve, said valve being mountable, at least partially, into said internal bore of said ferrule, said valve having an internal cavity with a sampling orifice located in a forward portion thereof and a movable sealing tip engageable with said orifice for opening and closing said orifice, said orifice having a longitudinal axis extending through a center thereof, and
 wherein said longitudinal axis of said orifice is generally parallel to and offset from the longitudinal axis of said internal bore.

26. The apparatus according to claim 25, wherein said longitudinal axis of said orifice is offset above said longitudinal axis of said internal bore.

27. The apparatus according to claim 26, wherein said internal cavity includes a drain passage having a forward portion extending forward to a front of the internal cavity and forming a bottom of said internal cavity, and wherein said drainage passage includes a bottom axis, said bottom axis being nonparallel and declining relative to the axis of the bore of the ferrule such that said bottom axis declines away from the front of the internal cavity such that material entering the internal cavity will drain down and out of the internal cavity.

28. An apparatus for moving a sample of a flowable material through a ferrule in a wall of a vessel or conduit comprising:
 a ferrule mounted in a wall of a vessel or conduit, said ferrule having an internal bore, said internal bore having a longitudinal axis;
 a valve, said valve being mountable, at least partially, into said internal bore of said ferrule, said valve having an internal cavity with a sampling orifice located in a forward portion thereof, said orifice having a longitudinal axis extending through a center thereof, and wherein said longitudinal axis of said orifice is generally parallel to and offset from the longitudinal axis of said internal bore,
 wherein said internal cavity includes a drain passage having a forward portion extending forward to a front of the internal cavity and forming a bottom of said internal cavity, and wherein said drainage passage has a bottom axis, said bottom axis being nonparallel and declining relative to the axis of the bore of the ferrule such that said bottom axis declines away from the front of the internal cavity such that material entering the internal cavity will drain down and out of the internal cavity.

29. An apparatus for moving a sample of a flowable material through a ferrule in a wall of a vessel or conduit comprising:

a ferrule mounted in a wall of a vessel or conduit, said ferrule having an internal bore, said internal bore having a longitudinal axis;

a valve, said valve being mountable, at least partially, into said internal bore of said ferrule, said valve having an internal cavity with a sampling orifice located in a forward portion thereof, said orifice having a longitudinal axis extending through a center thereof, and wherein said longitudinal axis of said orifice is generally parallel to and offset from the longitudinal axis of said internal bore, wherein said longitudinal axis of said internal bore of said ferrule has an angle of inclination in a direction away from the vessel or conduit, said valve has a valve body, and said valve body includes an internal drainage path with an angle of declination in a direction away from the vessel or conduit greater than or equal to said angle of inclination of said longitudinal axis of said internal bore of said ferrule.

* * * * *